(12) United States Patent
Lewis et al.

(10) Patent No.: US 11,684,334 B2
(45) Date of Patent: Jun. 27, 2023

(54) METHODS AND SYSTEMS FOR PROTOCOL MANAGEMENT

(71) Applicant: GE Precision Healthcare LLC, Milwaukee, WI (US)

(72) Inventors: Chelsey Lewis, Waukesha, WI (US); Bradley Gabrielse, Brookfield, WI (US); Vignesha Ramegowda, Pewaukee, WI (US); Sharon Ghelman, Hollywood, FL (US); Michael Sarju Vaz, Milwaukee, WI (US); Ryan Christopher Forbes, Waukesha, WI (US); Maud Bonnard, Brookfield, WI (US); Benjamin Thomas Hauser, Winston-Salem, NC (US); Elisa Pertuset, Hatboro, PA (US)

(73) Assignee: GE Precision Healthcare LLC, Milwaukee, WI (US)

( * ) Notice: Subject to any disclaimer, the term of this patent is extended or adjusted under 35 U.S.C. 154(b) by 849 days.

(21) Appl. No.: 16/553,028

(22) Filed: Aug. 27, 2019

(65) Prior Publication Data

US 2021/0059631 A1 Mar. 4, 2021

(51) Int. Cl.
| | |
|---|---|
| *G16H 40/40* | (2018.01) |
| *A61B 6/00* | (2006.01) |
| *G06F 21/31* | (2013.01) |
| *G06F 21/84* | (2013.01) |
| *G06F 9/54* | (2006.01) |
| *G16H 40/63* | (2018.01) |

(52) U.S. Cl.
CPC .............. *A61B 6/54* (2013.01); *A61B 6/5205* (2013.01); *G06F 9/542* (2013.01); *G06F 21/31* (2013.01); *G06F 21/84* (2013.01); *G16H 40/40* (2018.01); *G16H 40/63* (2018.01); *G06F 2221/2149* (2013.01)

(58) Field of Classification Search
CPC .................................................. G06F 3/0482
See application file for complete search history.

(56) References Cited

U.S. PATENT DOCUMENTS

| | | | |
|---|---|---|---|
| 9,285,482 B2 * | 3/2016 | Vourc'h | G01S 19/20 |
| 10,470,739 B2 | 11/2019 | Raman et al. | |
| 10,849,585 B1 * | 12/2020 | Teixeira | G06N 3/08 |
| 2006/0119622 A1 * | 6/2006 | Kariathungal | G16H 40/63 |
| | | | 345/653 |
| 2012/0227000 A1 * | 9/2012 | McCoy | G06F 3/0482 |
| | | | 715/762 |
| 2014/0128941 A1 * | 5/2014 | Williams | A61N 5/06 |
| | | | 315/193 |
| 2015/0227702 A1 * | 8/2015 | Krishna | A61B 5/7257 |
| | | | 705/2 |

(Continued)

*Primary Examiner* — Di Xiao
(74) *Attorney, Agent, or Firm* — McCoy Russell LLP

(57) ABSTRACT

Various methods and systems are provided for generating a guided workflow and assisting in clinical decision making during operation of an imaging system at a site. Via a protocol manager interface, displaying a default protocol generated for the imaging system by a manufacturer, an authorized user may customize the protocol for the site. A workflow, in accordance with the modified protocol, is then displayed to another non-authenticated user at a time of operating the imaging system for an active scan.

18 Claims, 12 Drawing Sheets

(56) References Cited

U.S. PATENT DOCUMENTS

| | | | |
|---|---|---|---|
| 2015/0261923 A1* | 9/2015 | Medow | A61M 5/1723 |
| | | | 705/2 |
| 2017/0202534 A1* | 7/2017 | Crotty | A61B 6/465 |
| 2017/0227660 A1* | 8/2017 | Zhang | A61B 6/563 |
| 2019/0232070 A1* | 8/2019 | Lancaster | A61N 1/3931 |

* cited by examiner

FIG. 5

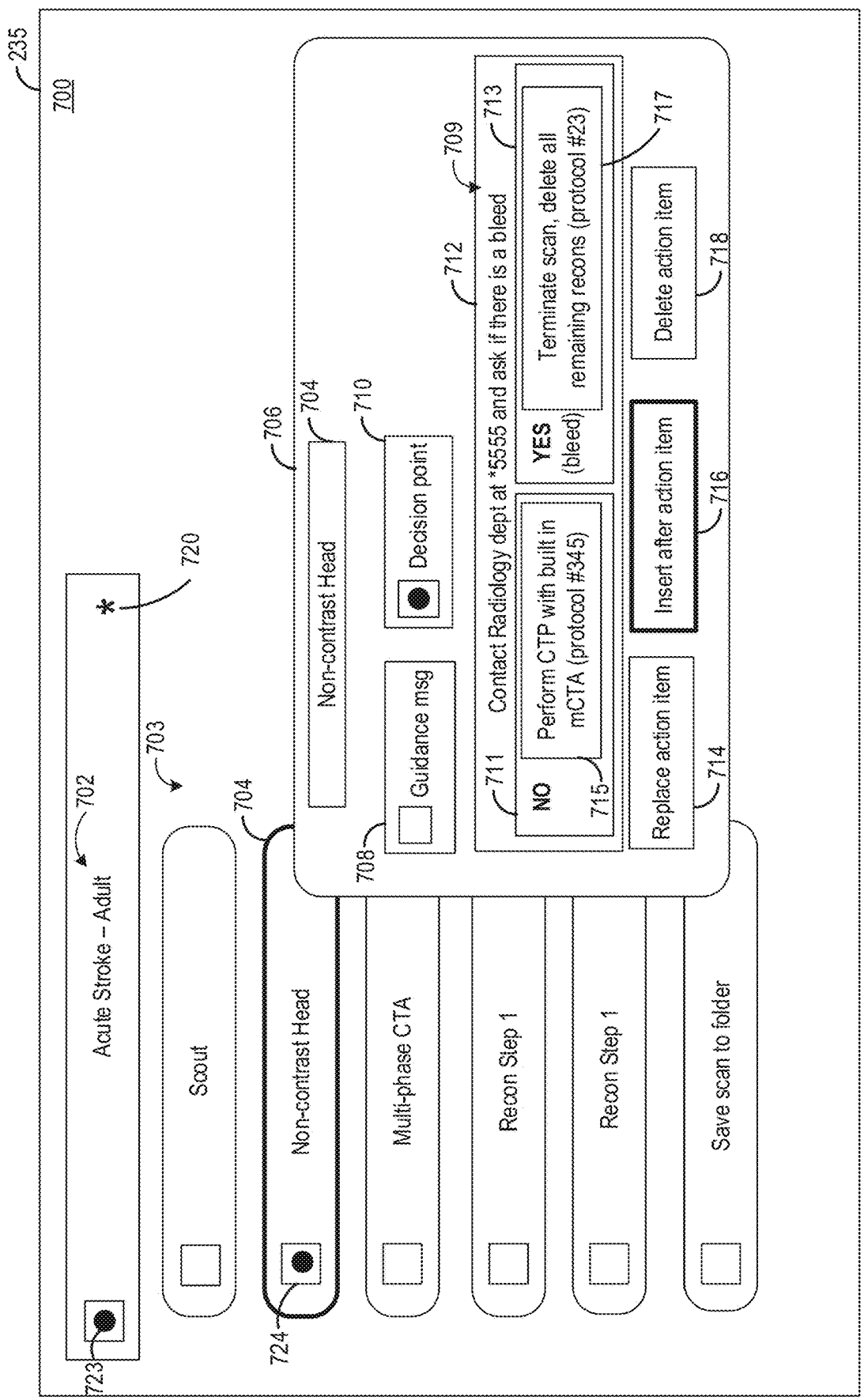

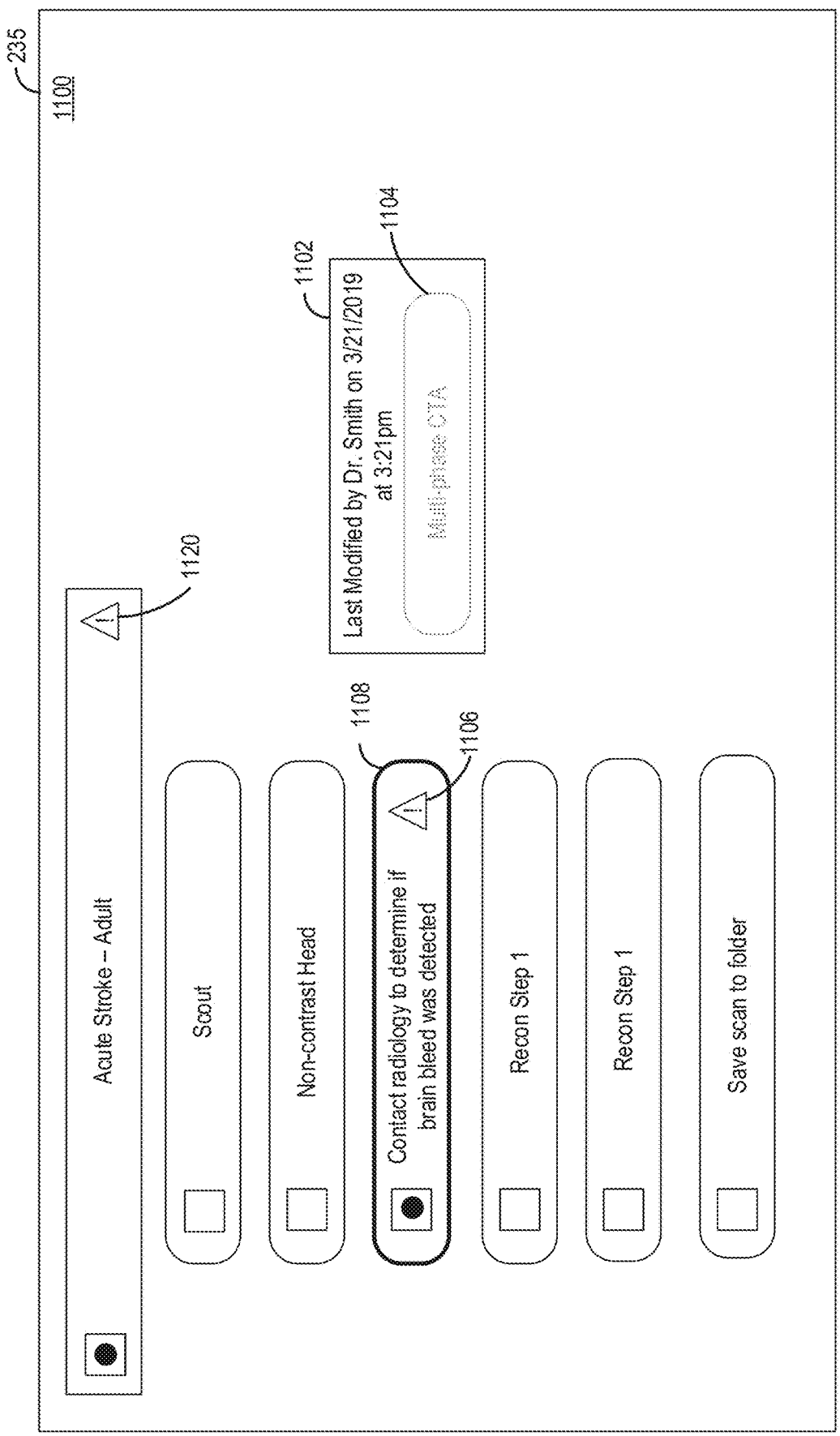

METHODS AND SYSTEMS FOR PROTOCOL MANAGEMENT

FIELD

Embodiments of the subject matter disclosed herein relate to management of workflow in healthcare and diagnostic protocols.

BACKGROUND

Medical imaging diagnostic workflows typically include multiple protocols for a given suspected clinical issue. During an active scan, a technologist has to pick an initial protocol to start with, and at a decision point of the protocol, may have to update subsequent action items of the protocol or switch to another protocol. The switch may be defined by clinical rules which may be site specific, issue specific, imaging modality specific, etc. The technologist has to refer to manuals and handbooks during the active scan to identify the decision points, an appropriate response, and identify a subsequent protocol to execute. In addition, the technologist has to select settings for the imaging system being operated based on the protocol selection. In some cases, the initial protocol may be a default protocol that includes details from all related protocols, to cover all possible scenarios, and the technologist has to identify and manually remove the inapplicable steps from the protocol during the active scan.

BRIEF DESCRIPTION

In one embodiment, a system comprises a display; and a computing device operably coupled to the display and storing instructions executable to: output, to the display, a protocol manager interface including a default protocol for an imaging system, the default protocol including one or more action items to be executed in a sequence during an imaging scan by the imaging system, at least a portion of the one or more action items specifying imaging system parameters for the imaging scan; responsive to input from an authenticated user, modify the default protocol including modifying the one or more action items and/or the sequence; store the modified protocol in a memory of the computing device; and responsive to a subsequent request to perform the imaging scan, retrieve the modified protocol and operate the imaging system in accordance with the imaging system parameters defined in the modified protocol.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 5 shows an example protocol selection by a scan technologist, manually, based on clinical rules;

FIGS. 7 and 8 show an example protocol manager interface for receiving input from an authenticated user to modify an action item of a default protocol;

FIG. 11 shows an example protocol manager interface displaying the modified protocol of FIG. 7 in a protocol library.

DETAILED DESCRIPTION

Figure 1:
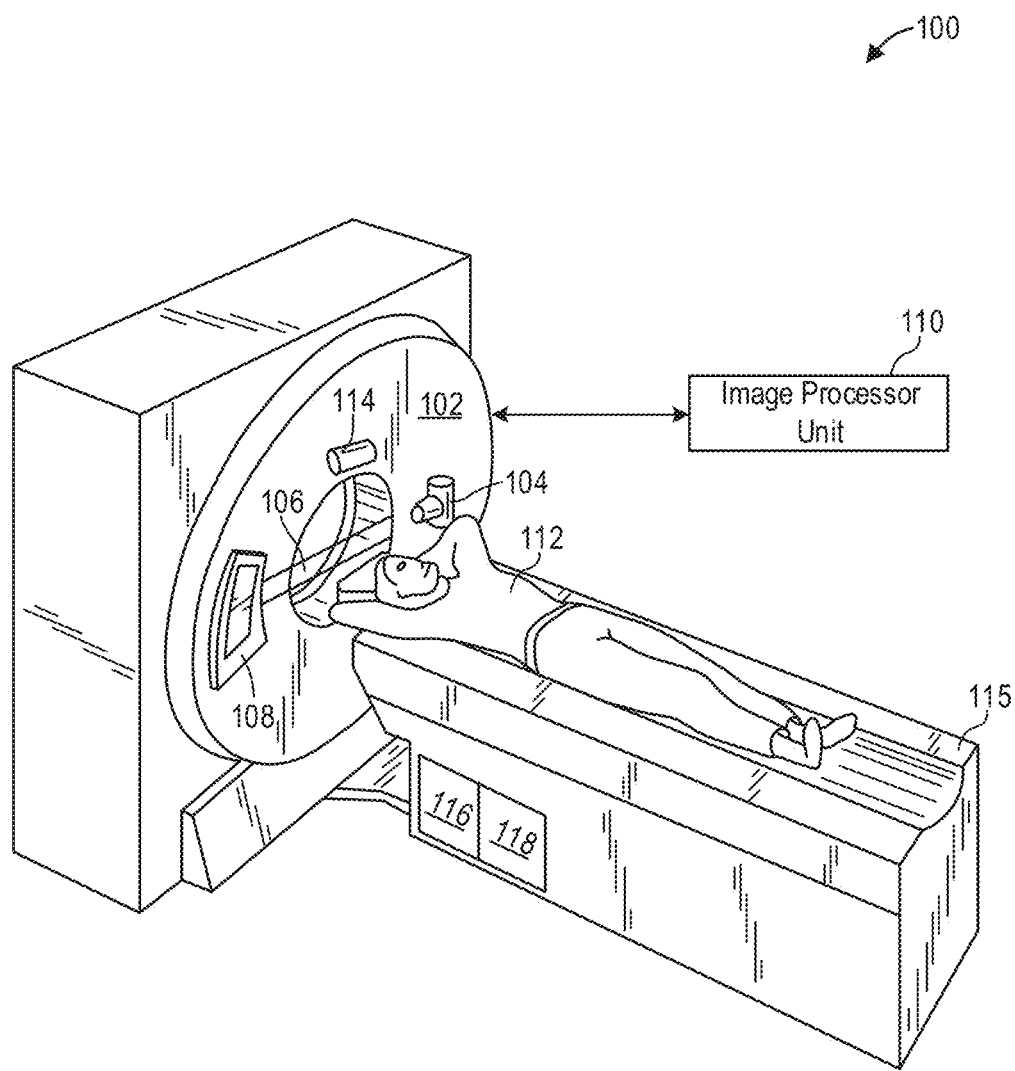
FIG. 1 shows a pictorial view of an imaging system according to an embodiment.

The following description relates to various embodiments of protocol management and clinical decision support systems. In particular, systems and methods are provided for enabling modification of a manufacturer-installed default protocol, associated with an imaging system, by an authenticated user. The systems and method further enable the modified protocol to be retrieved for providing a guided workflow to a non-authenticated scan technologist operating the imaging system when scanning for a suspected clinical disorder. During the operation of certain imaging modalities, such as computed tomography (CT) imaging, a scan technologist may not know ahead of time what the final scan protocol will be. The scan technologist may start with a default protocol for the suspected clinical disorder, and then, in-flight, manually select one of a plurality of exam protocol branches for the patient based on clinical rules. This may include the technologist having to retrieve information, guidance, and/or other imaging data for the given patient from other sources (e.g., another group of the healthcare system, another imaging modality, etc.) and then making a decision as to which protocol branch to subsequently select based on the retrieved information. As an example, the technologist may have to rely on the results of an angiogram being analyzed by a cardiologist before deciding whether to proceed with perfusion imaging. Errors in protocol selection by the scan technologist can result in a medical issue not being diagnosed correctly. As an example, if the technologist does not correctly categorize the size of the patient, an incorrect protocol may be selected, and the imaging system settings may be incorrectly applied. With reference to a computed tomography (CT) imaging system, table position settings, gantry position settings, and X-ray source voltage and current settings, may be incorrectly applied. For example, table and gantry settings for an abdominal scan may be different for a patient deemed to be "small" versus "large" or "medium". As a result, the decision making process may be subjective and inconsistent from technologist-to-technologist, as well as patient-to-patient for the same technologist. As such, the process adds significant cognitive load on the technologist, especially in trauma use cases where there may be a limited amount of time in which to make critical medical decisions.

Thus, according to embodiments disclosed herein, a guided diagnostic workflow can be automatically generated, reducing the cognitive load on a scan technologist at the time of an active scan. An authorized lead technologist can modify a default protocol for an imaging system, such as one provided by a manufacturer, customizing the protocol for the site, the imaging modality, and/or other parameters. The modifications may be enabled via interactions with a protocol manager interface executed on a computing device. The modifications may not only specify a type of scan to be executed, but also a sequence of actions to be performed at the time of the scan, as well as imaging systems settings such as power settings, position settings, motor speed settings, etc. At the time of a scan, the protocol manager interface may retrieve the modified protocol and provide a guided workflow to the scan technologist with each action item of the modified protocol representing a corresponding action item to be performed during the workflow. The modifications to the protocol may be in the form of prompts that pop-up during the workflow to provide step-by-step instructions for executing a linked action item. In addition, the prompts may assist in scouting a patient, such as for size and issue, so that protocol selection is facilitated. The modifications may also be in the form of a decision point with predefined responses, each response linked to a downstream protocol with a distinct set of action items. Selection of a response by the scan technologist during the active scan automatically updates the workflow with the appropriate actions items to be subsequently performed. In other words, a pre-built workflow is delivered to the scan technologist once a decision is made, and the scan technologist can complete the active scan in accordance with the provided workflow. In addition, the protocol manager interface may automatically apply (or define) the imaging system settings defined in the protocol or protocol branch that was selected. As a result, subjectivity in decision making (e.g., technologist selection of patient size category) as well as inconsistencies in a workflow, such as human-to-human variability in manually updating a protocol and selection of appropriate imaging system settings, are reduced. This may be of particular interest in trauma use cases where protocol section and imaging settings can be expedited without affecting scan reliability.

For example, a computing device of an imaging system may be configured with a protocol manager which outputs a protocol manager interface on a display. A first interface may be displayed to an authenticated user (such as a user whose authentication is received and confirmed) to enable the user to modify a default protocol for an imaging system, the default protocol selected from a library, and the protocol including one or more action items to be executed in a sequence during an imaging scan by the imaging system. At least a portion of the one or more action items may specify imaging system parameters for the imaging scan. Responsive to input from the authenticated user (that is, a person who does have permission to modify a protocol), such as a lead technologist at an imaging site (e.g., healthcare facility), the protocol manager modifies the default protocol including modifying the one or more action items and/or the sequence. The modified protocol is then stored in a memory of the computing device. Responsive to a subsequent request to perform a new imaging scan task, such as requested by the authenticated user or another non-authenticated user (such as a user whose authentication is received and who does not have permission to modify the protocol, e.g., a scan technologist at the site), the protocol manager may retrieve the modified protocol and display a workflow to be executed during the imaging scan. The workflow comprises the one or more action items of the modified protocol. In addition, the imaging system may be operated in accordance with the imaging system parameters defined in the modified protocol, such as power settings and motor settings defined in the modified protocol.

In one example, the default protocol is a manufacturer installed default protocol installed on the computing device at the time of imaging system manufacture. The protocol manager may be further configured with instructions that push a notification to the manufacturer of the imaging system responsive to the authenticated user modifying the protocol. The notification may include the modified protocol and a comparison of the modified regions in relation to the default protocol.

In some examples, the input from the authenticated user includes selection, on the protocol manager interface, of an action item from the one or more action items. Responsive to the input from the authenticated user, the protocol manager may output, to the display, a message box associated with the selected action item. Content is then received in the displayed message box from the authenticated user. The content may include tasks to be executed at a defined point of the corresponding workflow during an imaging scan, such as a notification reminding the person performing the scan of a specific person or specific department of the site to contact, as well as the relevant contact number (e.g., "contact radiology department at *5555", or "contact Dr. Smith at Cardiology at *4444"). The selected action item of the modified protocol is automatically populated the received content while the existing content is removed from the selected action item. As a result, when performing the imaging scan, a workflow is output with the selected action item displaying the received content. The received content may also specify one or more new action items to be linked downstream of the selected action item such that upon receiving the content, all action items of the default protocol that are located downstream of the selected action item are automatically removed. Further, the modified protocol is populated with the one or more new action items downstream of the selected action item. As a result, when performing the imaging scan, the workflow that is output includes the one or more new action items displayed downstream of the selected action item.

In some examples, the displayed message box further includes category elements categorizing the modification to the selected action item, the category elements including at least a first category element associated with a guidance message and a second category element associated with a decision point (e.g., "Bleed?"). The displayed message box prompts the authenticated user to select one of the first and second category elements. If the second category element is selected, the received content includes a first set of new action items (e.g., "Perform perfusion") associated with a first response element (e.g., "No") of the decision point and a second, different set of new action items (e.g., "do not perform perfusion") associated with a second response element of the decision point (e.g., "Yes"). At a time of the imaging scan, the interface may display a prompt asking the non-authenticated user to select one of the first and second response elements and responsive to selection, the workflow output on the interface may be updated. For example, selection of the first response element may cause the protocol manager to output, on the interface, an updated workflow with the first set of new action items displayed downstream of the selected action item while removing all action items of the default protocol downstream of the selected action item and while not displaying any of the second set of actions items. In comparison, selection of the second response element may cause the protocol manager to output, on the interface, an updated workflow with the second set of new action items displayed downstream of the selected action item while removing all action items of the default protocol downstream of the selected action item and while not displaying any of the first set of actions items.

The modified protocol is then stored in a protocol library as a function of the default protocol. In some examples, a visual attribute of the stored modified protocol may be updated to distinguish the modified protocol from the default protocol in the protocol library. For example, an identification key may be provided. Additionally, a visual attribute of the one or more modified action items may be changed, such as a border color, font type, font color, background color, etc.

Figure 2:
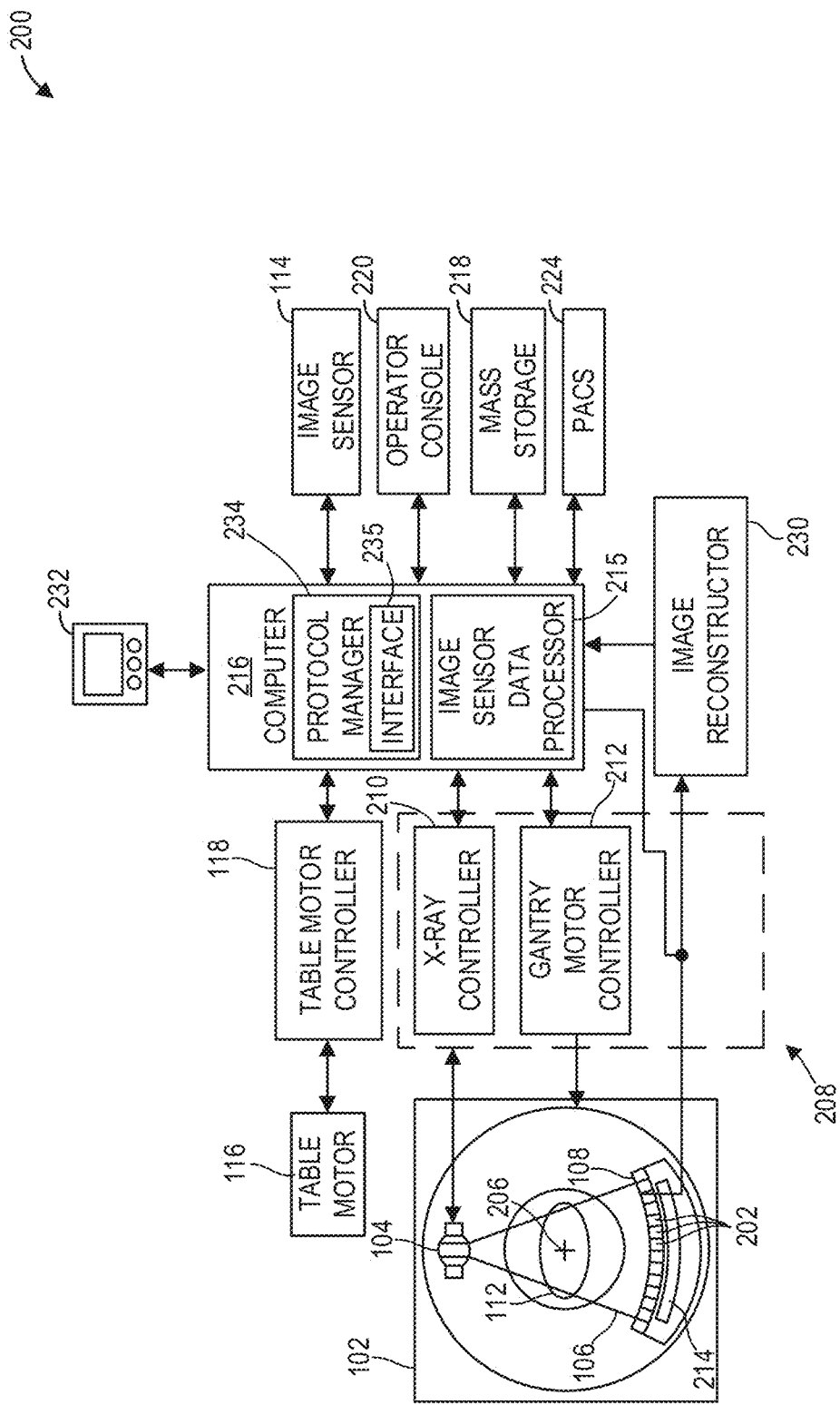
FIG. 2 shows a block schematic diagram of an exemplary imaging system according to an embodiment.
Figure 3:
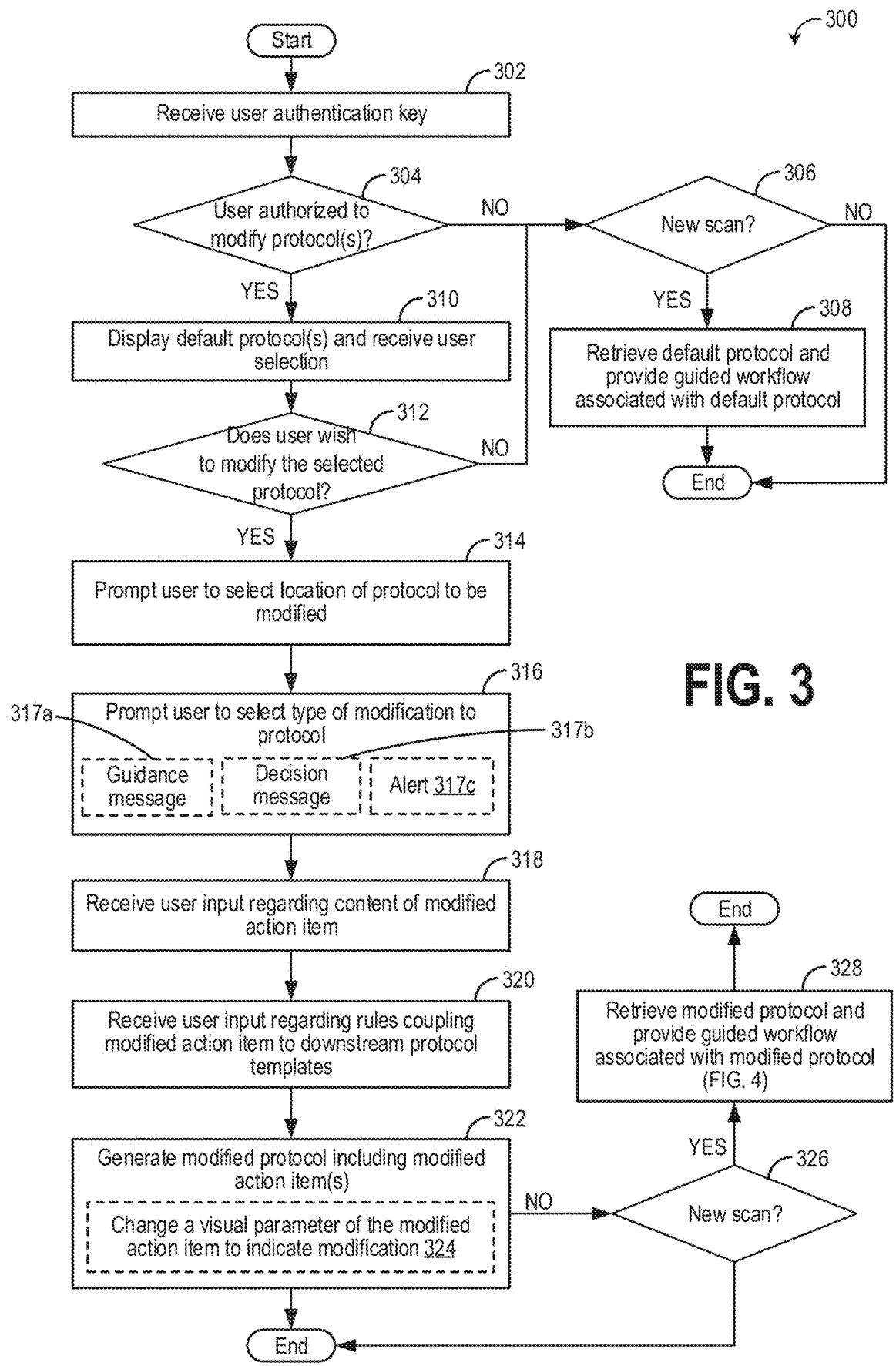
FIG. 3 shows an example method for modifying a default protocol of an imaging system based on input from an authenticated user.
Figure 4:
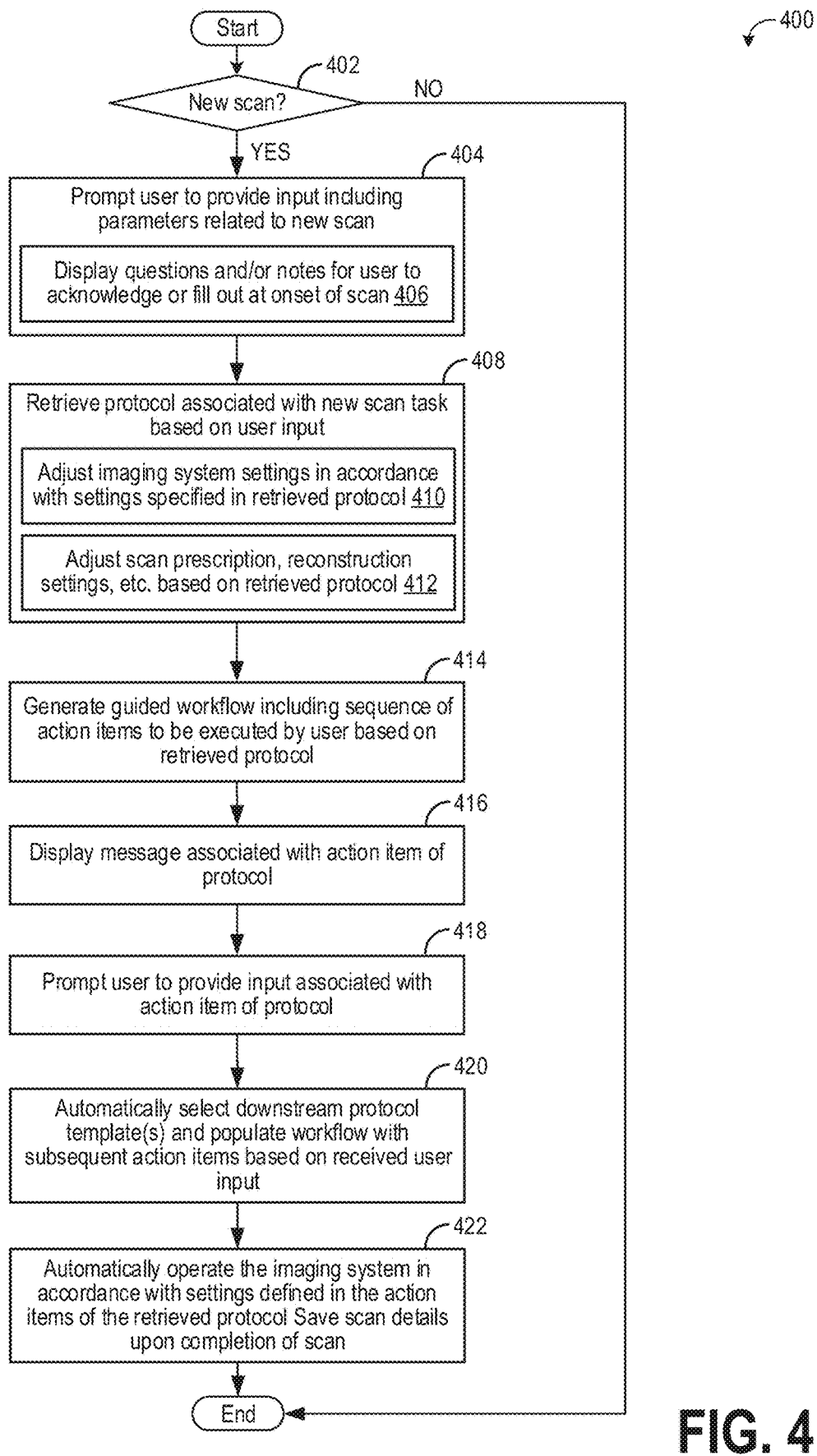
FIG. 4 shows an example method for generating a guided workflow during operation of the imaging system, in accordance with a modified protocol.
Figure 6A:
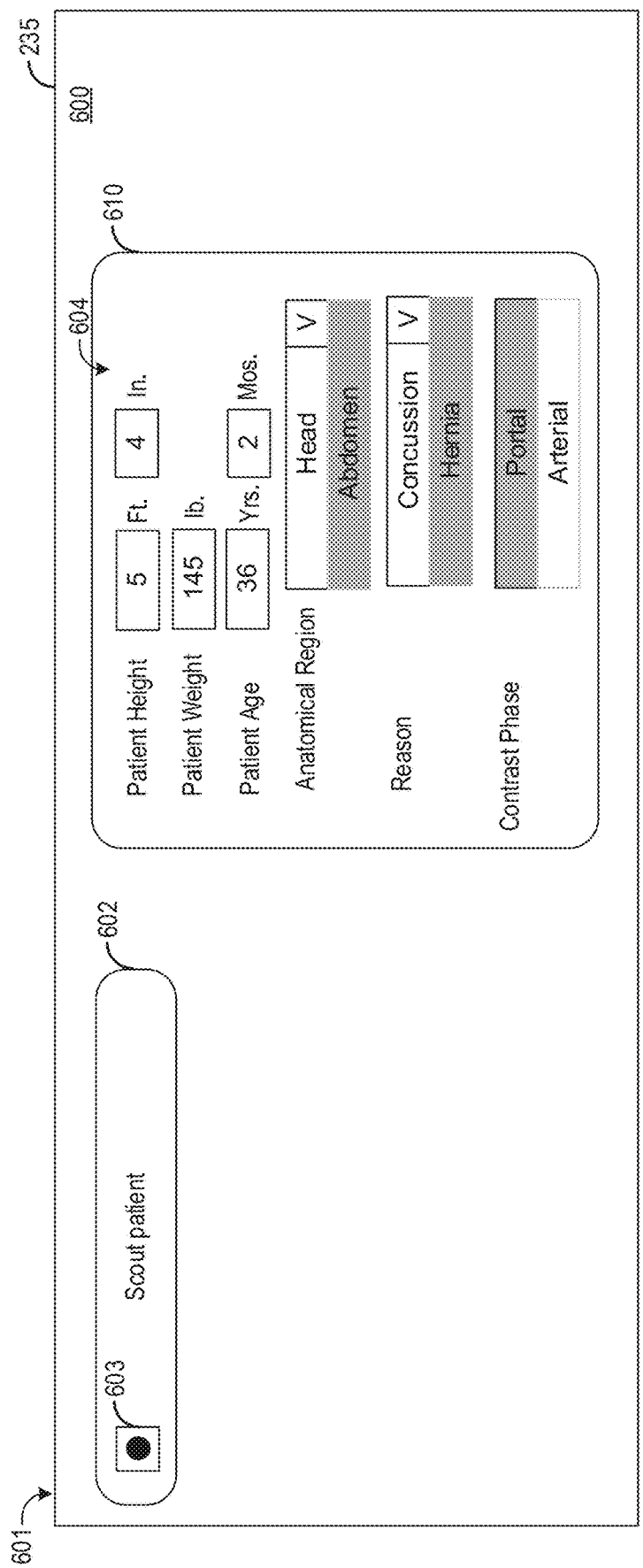
FIGS. 6A and 6B shows an example protocol manager interface for facilitating protocol selection by a scan technologist.
Figure 6B:
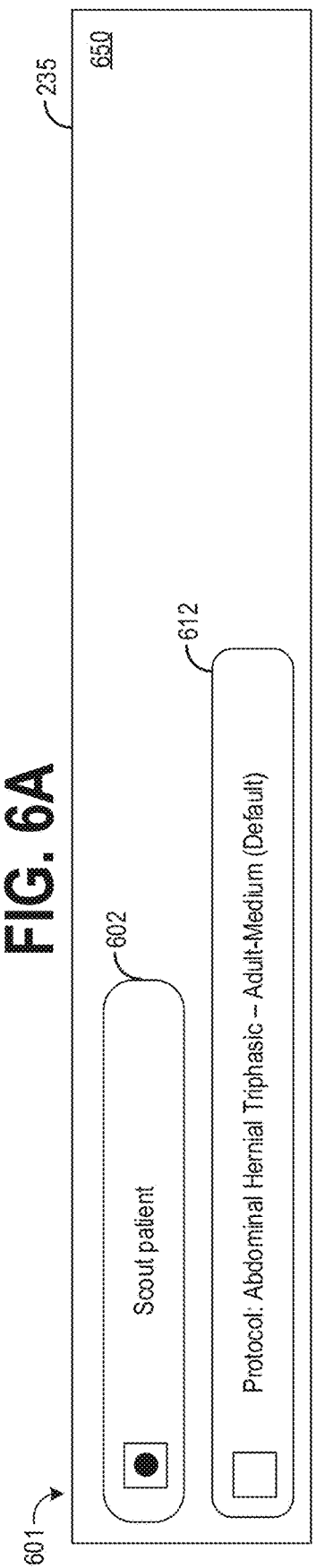
Figure 8:
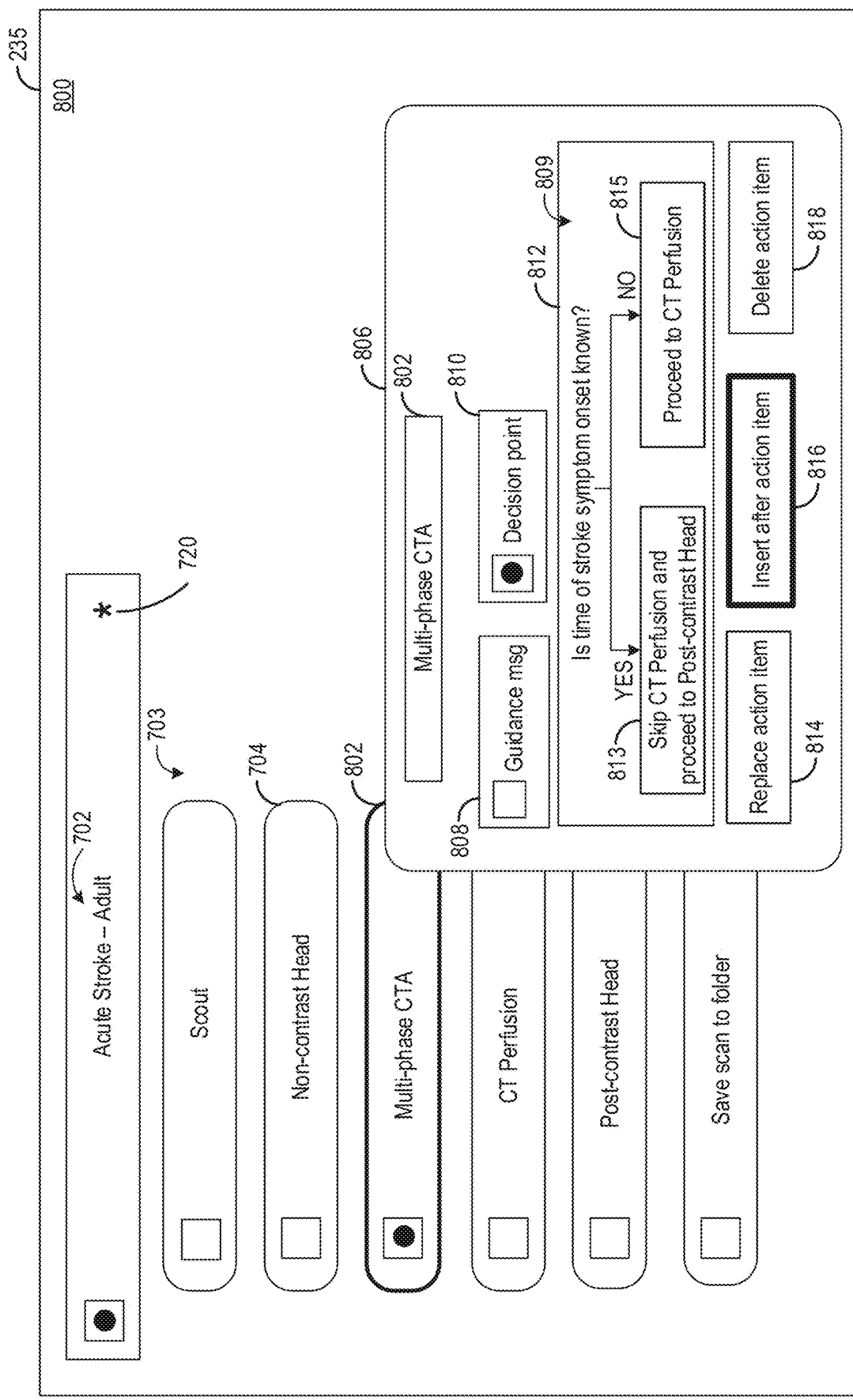
Figure 9A:
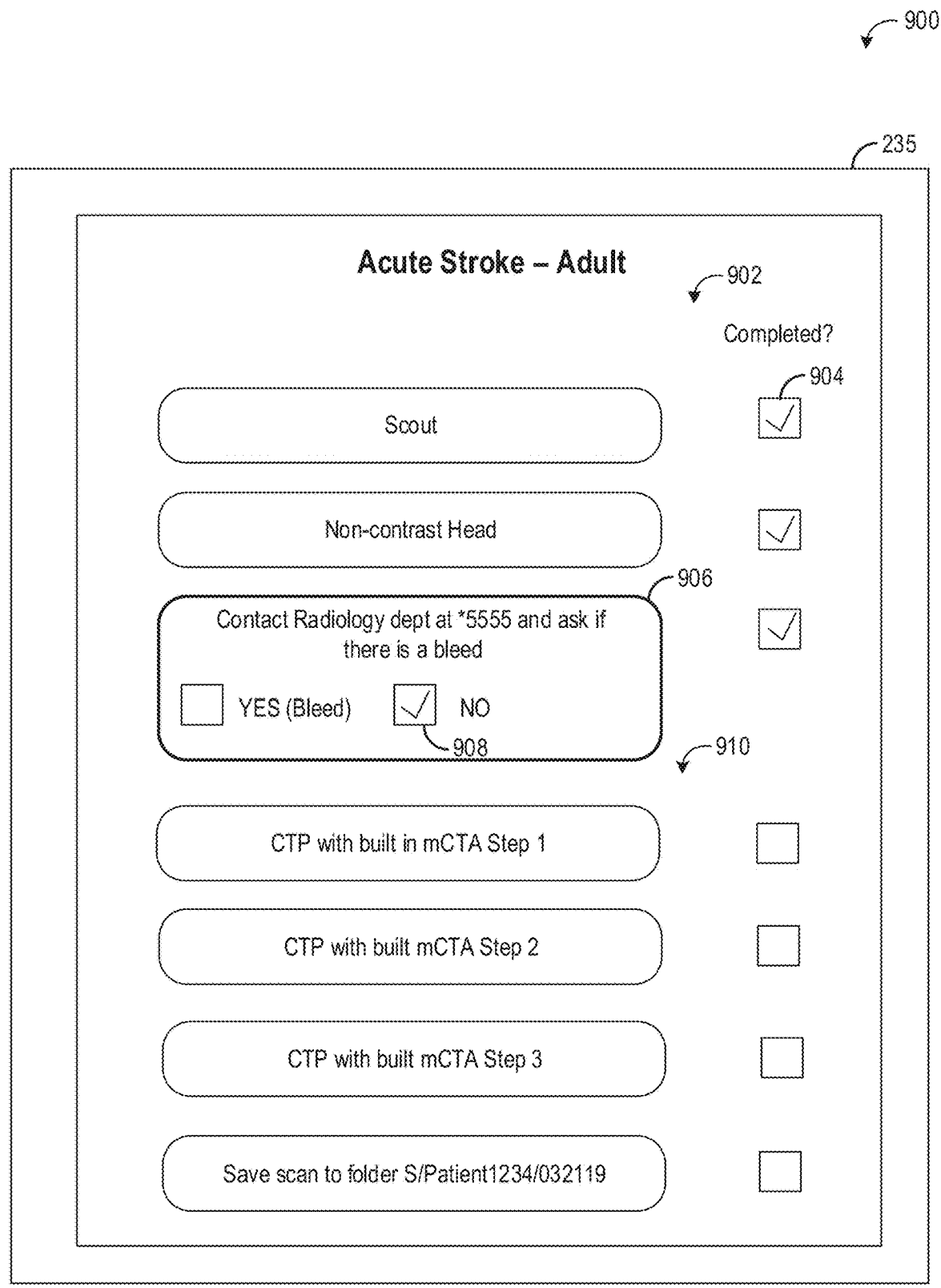
FIGS. 9A and 9B show example protocol manager interfaces for displaying a guided workflow to a non-authenticated user based on user response selection to the decision point introduced in the modified protocol of FIG. 7.
Figure 9B:
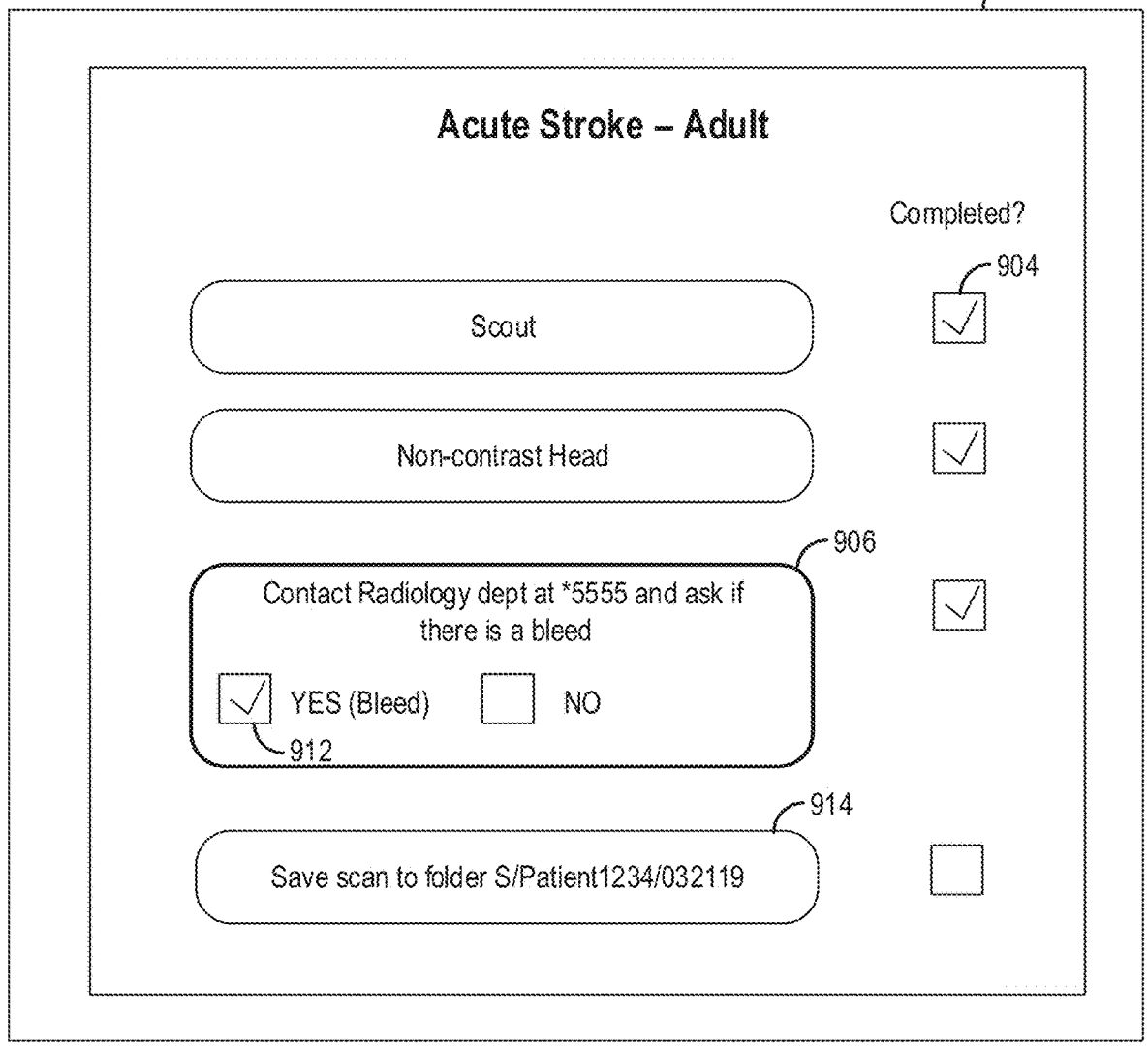
Figure 10:
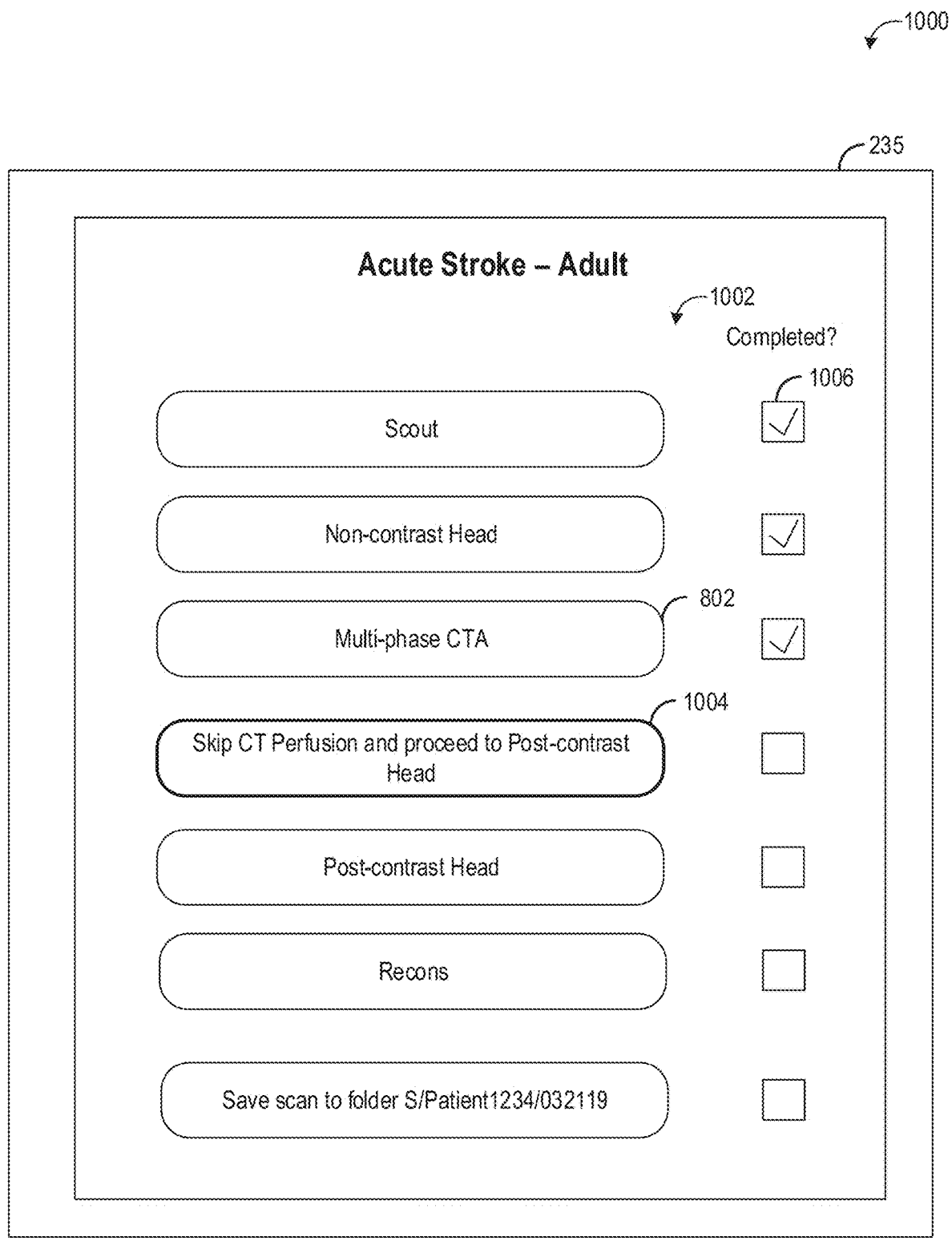
FIG. 10 shows an example protocol manager interface for displaying a guided workflow to a non-authenticated user based on the modified protocol of FIG. 8.

An example medical imaging system in the form of a CT imaging system that may be used by a scan technologist to acquire images of a patient is provided in FIG. 1. The imaging system may include a protocol manager, as shown at FIG. 2, for guiding the scan technologist through the various steps of the imaging protocol, as well as providing guidance and automation at decision points. FIG. 3 shows a high level flow chart for enabling a lead technologist to modify one or more default protocols stored in a protocol library (such as the library of FIGS. 5 and 11). FIG. 4 shows a high level flow chart for guiding a scan technologist through a workflow generated responsive to protocol selection during an imaging session of the CT imaging system. Example user interfaces enabling an authenticated user to make modifications to a default protocol, to thereby generate a modified protocol, are shown at FIGS. 7 and 8. Example user interfaces guiding a non-authenticated user to through a protocol selection process is shown at FIGS. 6A-6B. Example user interfaces displaying a guided workflow, based on a modified protocol, to a non-authenticated user at a time of scanning are shown at FIGS. 9A, 9B, and 10. FIG. 11 shows an example modified protocol stored in a protocol library.

Though a CT system is described by way of example, it should be understood that the present techniques may also be useful when applied to imaging sessions with other imaging modalities, such as a positron emission tomography imaging system, a nuclear medicine imaging system, a magnetic resonance imaging system, an X-ray radiography imaging system, an X-ray fluoroscopy imaging system, an interventional imaging system (e.g., angiography, biopsy), an ultrasound imaging system and so forth. The present discussion of a CT imaging modality is provided merely as an example of one suitable imaging modality.

FIG. 1 shows example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 illustrates an exemplary CT system 100. Particularly, the CT system 100 is configured to image a subject 112 such as a patient, an inanimate object, one or more manufactured parts, and/or foreign objects such as dental implants, stents, and/or contrast agents present within the body. Throughout the disclosure, the terms subject and patient may be used interchangeably, and it is to be understood that a patient is one type of subject that may be imaged by the CT system, and that a subject may include a patient, at least in some examples. In one embodiment, the CT system 100 includes a gantry 102, which in turn may further include at least one X-ray radiation source 104, such as an X-ray generator, X-ray tube or X-ray source, configured to project a beam of X-ray radiation 106 for use in imaging the patient. Specifically, the X-ray radiation source 104 is configured to project the X-rays 106 toward a detector array 108 positioned on the opposite side of the gantry 102. Although FIG. 1 depicts only a single X-ray radiation source 104, in certain embodiments, multiple radiation sources may be employed to project a plurality of X-rays 106 for acquiring projection data corresponding to the patient at different energy levels. In some examples, multiple radiation sources may be placed at any point along the circumference of the gantry and each radiation source may have a detector or part there-of on the opposite side of the gantry.

In some examples, CT system 100 may include an imaging sensor 114 positioned on or outside the gantry 102. As shown, the imaging sensor 114 is positioned on an external side of the gantry 102 and orientated to image the subject 112 when the subject is at least partially outside the gantry 102. The imaging sensor 114 may include a visible light sensor and/or and an infrared (IR) sensor that includes an IR light source. The IR sensor may be a three-dimensional depth sensor such as a time-of-flight (TOF), stereo, or structured light depth sensor operable to generate three-dimensional depth images, while in other implementations the infrared sensor may be a two-dimensional IR sensor operable to generate two-dimensional IR images. In some implementations, a two-dimensional IR sensor may be used to infer depth from knowledge of IR reflection phenomena to estimate three-dimensional depth. Whether the IR sensor is a three-dimensional depth sensor or a two-dimensional IR sensor, the IR sensor may be configured to output a signal encoding an IR image to a suitable IR interface, which may be configured to receive the signal encoding the IR image from the IR sensor. In other examples, the imaging sensor may further include other components, such as a microphone to enable the reception and analysis of directional and/or non-directional sounds coming from an observed subject and/or other sources.

In certain embodiments, the CT system 100 further includes an image processing unit 110 configured to reconstruct images of a target volume of the patient using a suitable reconstruction method, such as an iterative or analytic image reconstruction method. For example, the image processing unit 110 may use an analytic image reconstruction approach such as filtered back-projection (FBP) to reconstruct images of a target volume of the patient. As another example, the image processing unit 110 may use an iterative image reconstruction approach such as adaptive statistical iterative reconstruction (ASIR), conjugate gradient (CG), maximum likelihood expectation maximization (MLEM), and model-based iterative reconstruction (MBIR), and so on to reconstruct images of a target volume of the patient.

CT system 100 further includes a table 115 on which a subject to be imaged may be positioned. The table 115 may be motorized so that the vertical and/or lateral position of the table may be adjusted. Accordingly, table 115 may include a motor 116 and a motor controller 118. The table motor controller 118 moves the table 115 by adjusting the motor 116 for appropriately positioning the subject in the gantry 102 for acquiring projection data corresponding to the target volume of the subject. Table motor controller 118 may adjust both the elevation of table 115 (e.g., the vertical position relative to a ground on which the table sits) and lateral position of table 115 (e.g., the horizontal position of the table along an axis parallel to a rotational axis of the gantry).

FIG. 2 illustrates an exemplary imaging system 200 similar to the CT system 100 of FIG. 1. In one embodiment, the system 200 includes the detector array 108 (see FIG. 1). The detector array 108 further includes a plurality of detector elements 202 that together collect the X-ray beams 106 (see FIG. 1) that pass through the subject 112 to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 112 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the X-ray radiation source 104. In certain embodiments, the control mechanism 208 further includes an X-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (or computer) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device. The storage device may be internal or external to computing device 216. In still further examples, the data may be transmitted by the computing device to a cloud-based server for storage. While only a single computing device 216 is illustrated in FIG. 2, in some examples computing device 216 may be distributed across multiple physical devices.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

As described further herein, the computing device 216 uses the operator-supplied and/or system-defined commands and parameters to operate the table motor controller 118, which in turn, may control the motorized table 115. For example, the computing device 216 may send commands to the motor controller 118 instructing the motor controller 118 to adjust the vertical and/or lateral position of the table 115 via the motor 116.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

Computing device 216 may further store instructions for (e.g., in mass storage 218), and may be configured to execute (e.g., via a processor), a protocol manager 234. Protocol manager 234 generates an interface, referred to herein as a protocol manager interface 235, to assist an operator of system 200 with protocol management. Imaging system 200 may be configured with a default protocol, such as a manufacturer installed default protocol, the default protocol stored in the mass storage 218. In one example, there may be multiple default protocols (e.g., a library of default protocols, as discussed with reference to FIG. 5), each default protocol associated with a different issue, a different body part being scanned, a different patient size, combinations thereof, etc. For example, a first default protocol may be provided for scanning a mid-sized adult's abdomen for signs of bleeding. A different default protocol may be provided for scanning a child's head for signs of concussion, and so on. Each default protocol may include settings for system 200, such as settings for the gantry motor, the X-ray source, the table motor, etc. The protocol may include multiple action items that are executed in a defined sequence. A scan technologist retrieves the protocol and performs a workflow during the scan, wherein each step of the workflow is based on the multiple action items, and the sequence of the action items, as defined in the protocol.

As elaborated herein, the protocol manager 234 may enable an authenticated user, such as a lead technologist of a site at which the imaging system is being operated, such as a healthcare site (e.g., hospital, clinic, imaging facility, etc.), to make modifications to the default protocol(s). The authenticated user can customize the protocol manager settings and adjust the action items in the default protocol, thereby customizing the default protocol for the specific site (e.g., the specific healthcare or imaging facility). This allows the site to have maximum control over what instructions and messages they would like to present to a user (e.g., a scan technologist) at the time of a scan. In one example, the protocol is customized to account for site rules. An example method for modifying a default protocol based on input from an authenticated user is shown with reference to FIG. 3.

In some examples, the protocol manager may be stored and/or executed on a remote device in communication with computing device 216, such as on a central server (e.g., of the medical facility). User input from the authenticated user may be received at the system 200 and may be sent to the server. Modifications to the default protocol(s) by the authenticated user may also be saved on the server, and the server may output workflows to the display device of system 200 when requested. For example, if a modified protocol is retrieved from the server onto a local computing device (such as imaging client device) by a non-authenticated user at the time of a scan, a workflow is generated thereon in accordance with a modified protocol and imaging system parameters and settings are automatically applied in accordance with the modified protocol. The server also may communicate with more than one imaging system and/or imaging client device to enable a central library of protocols (including default and modified protocols) to be accessed from more than one imaging system.

The protocol manager interface 235 may enable the authenticated user to modify one or more action items and/or their sequence. As non-limiting examples, the user may alter the content of an existing action item, add a new action item, delete an action item, and/or add a new decision point in the default protocol. In one example, the newly added action item, or content altered action item, may generate a pop-up message on the display providing step-by-step instructions regarding a clinical task to be executed by a scan technologist at a defined point of an active scan. Alternatively, the modification may include an alert regarding an action that needs to perform at a defined point in the protocol (e.g., "retrieve angiogram from radiology department").

When a decision point is included, the authenticated user may also add in predefined response options to the decision point. The protocol manager may display a decision message at the decision point that requests user input (e.g., "which part of the subject's body is to be scanned?" or "is a contrast phase required?"). Each predefined response option may be linked to additional action items, or downstream protocol templates such that selection of a particular response option automatically populates the protocol with a defined set of new action items. For example, scan prescriptions, scan reconstructions, as well subsequent action items to be displayed at defined time points of the of remainder of the protocol may be automatically selected. Each modified action item of the modified protocol results in a corresponding modification to a workflow when executed by the scan technologist at the time of an active scan. For example, during the active scan, the modified protocol is retrieved by the protocol manager and the action items are displayed so that the scan technologist can execute a workflow in accordance with the modified protocol. At a decision point, a response selection is prompted, and upon receiving input from the scan technologist, the protocol manager automatically updates the protocol so that the workflow presented to the scan technologist is accordingly updated. As a result, a guided workflow is provided that reduces the cognitive load on the scan technologist. An example method for providing a workflow to a user, at the time of an active scan, based on a modified protocol is shown with reference to FIG. 4.

It will be appreciated that the storage device where the modified protocols are saved includes permanent memory. In some examples, when the non-authenticated user enters input to a protocol, per the prompts defined in the modified protocol by the authenticated user, the resultant workflow that gets generated based on that input may be stored in permanent memory. For example, the inputs/decisions made by the user may be saved, and these saved inputs/decisions and resulting protocols may be replayed at a later time, used for statistical analysis, or other purpose.

In some examples, the computing device 216 may include computer-readable instructions executable to send commands and/or control parameters to one or more of the DAS 214, the X-ray controller 210, the gantry motor controller 212, and the table motor controller 226 according to an exam imaging protocol that includes clinical task/intent of the exam. The commands sent may be further based on the protocol selection and protocol changes defined by protocol manager 234. For example, the clinical intent may inform on the goal of the procedure (e.g., general scanning or lesion detection, anatomy of interest, critical to quality (CTQ) parameters, or other goals) based on a clinical indication, and may further define the desired subject position and orientation during the scanning (e.g., supine and feet first). The operator of the system 200 may then position the subject on the table according to subject position and orientation specified by the imaging protocol. Further, the computing device 216 may set and/or adjust various scan parameters (e.g., dose, angle of gantry rotation, kV, mA, attenuation filters) according to the imaging protocol. The imaging protocol may be selected by the operator from among a plurality of imaging protocols stored in memory on the computing device 216 and/or a remote computing device, or the imaging protocol may be selected automatically by the computing device 216 according to received patient information, for example. Further still, the protocol may be dynamically adjusted during an active scanning or imaging session by the protocol manager 234.

Additionally, in some examples, computing device 216 may include an image sensor data processor 215 that includes instructions for processing imaging information received from an imaging sensor, such as sensor 114 of FIG. 1. The information received from the imaging sensor, which may include depth information and/or visible light information, may be processed to determine various subject parameters, such as subject identity, subject size, current subject position, subject movement, and/or subject emotional state. These subject parameters may be used by the computing device 216 or another suitable device to adjust various parameters of the medical imaging session, such as pausing image acquisition and/or outputting notifications to the subject and/or operator when subject movement is detected, as will be described in more detail below. Further, video stream(s) from the imaging sensor may be displayed via display 232.

The information from the image sensor may be usable by the image sensor data processor 215 to perform tracking of one or more subjects in the field of view of the image sensor. In one example, the image information (e.g., depth information) may be used to perform skeletal tracking, wherein a plurality of joints of the subject are identified and analyzed to determine movement, pose, position, etc., of the subject. The location of the joints during skeletal tracking may be used to determine the subject parameters described above.

The imaging system of FIGS. 1-2 may be operated in accordance with a protocol. Typically, a local computing device (such as computer 216) coupled to the imaging system may be installed with one or more default protocols stored in the memory (such as in mass storage 218). In one example, the one or more default protocols stored in the memory are manufacturer installed protocols provided as a library of protocols. The default protocols may be selectively configured for the associated imaging modality (such as for computerized tomography imaging, magnetic resonance imaging, positron emission tomography, etc.). The different default protocols may be associated with various imaging parameters, such as a medical condition being assessed for, a body part being scanned, patient characteristics, and combinations thereof. For example, a distinct protocol is provided for scanning a mid-sized adult's abdomen for signs of bleeding as compared to scanning a child's head for signs of concussion, and so on. Each default protocol may include settings for the imaging system (e.g., imaging system 200 of FIG. 2), such as settings for the gantry motor, the X-ray source, the table motor, etc.

Figure 5:
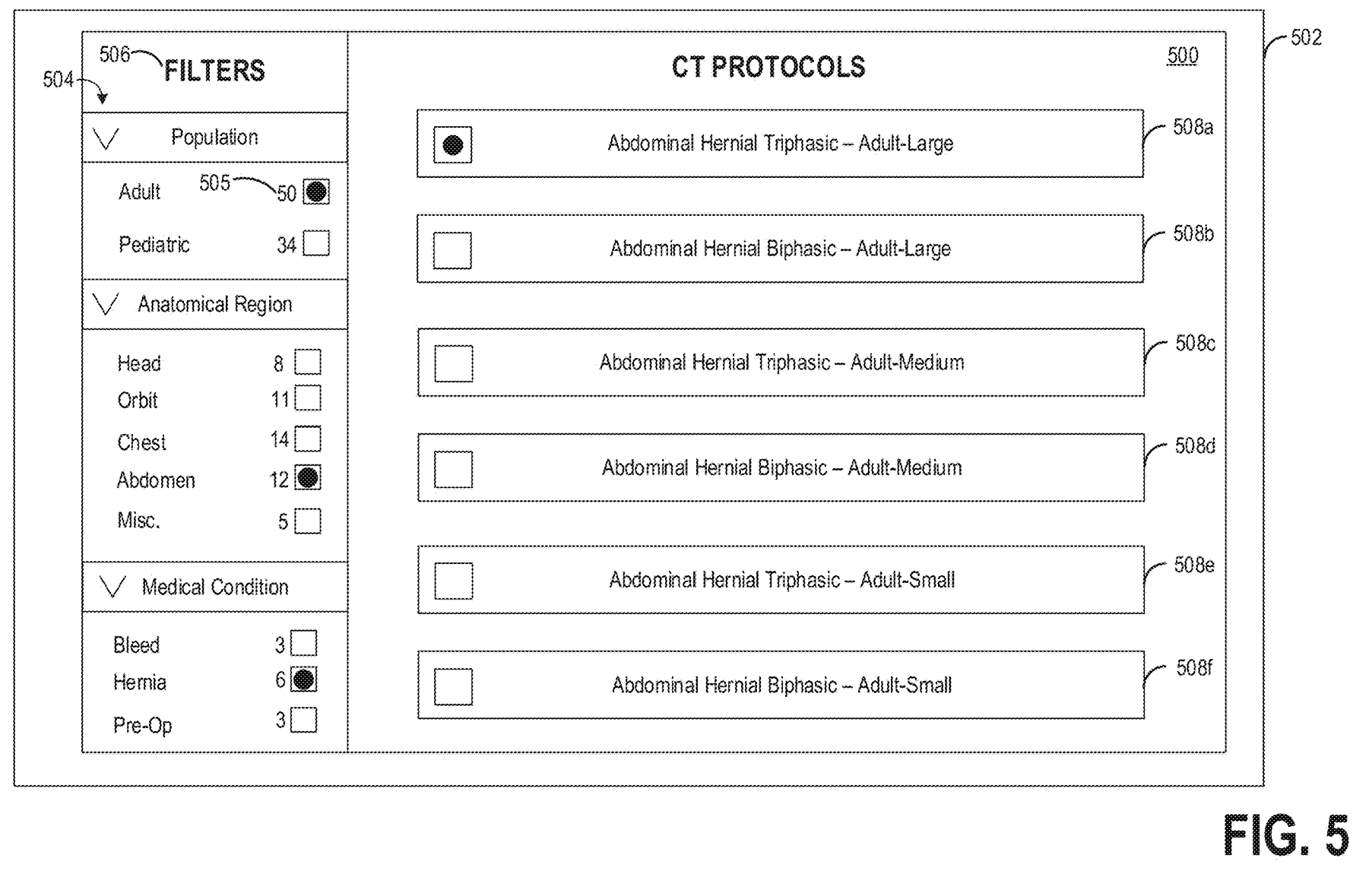

FIG. 5 shows as an example protocol library 500 including multiple default protocols that may be stored in the memory of a computing device of a CT imaging system. As described earlier, each protocol includes a series of action items, performed in a defined sequence. An operator operating the CT imaging system (e.g., a scan technologist) may, at the time of the scan, select a default protocol. The action items of the selected protocol are then used as guidelines by the operator during the scan.

The protocol library 500 may be displayed to the scan technologist on a display device, in the form of an interactive interface 502. Each protocol may be tagged with a plurality of attributes 504. A number of protocols having a selected attribute may be indicated by a marker 505. In the depicted example, the selectable attributes include population type, anatomical region, and medical condition. However, multiple other attributes may be included, such as phase contrast being used, type of scanning head being used, etc. At the onset of a new scan task, the scan technologist operating the imaging system shortlists default protocols from the library of protocols 500 by applying one or more filters 506. Each filter 506 selects for a specific attribute. By applying the filters 506, default protocols that do not have the selected attribute are not displayed, while default protocols which do have the selected attribute are compiled into a list for display.

In the depicted example, the scan technologist applies a filter for population type of the subject who is to be scanned, herein selecting for "adult" population. A further filter is applied for the anatomical region of the subject being scanned, herein selecting for "abdomen". Another filter is applied for medical condition being assessed, herein selecting for "hernia" (or herniated condition of the selected anatomical region). As a result of the selected filters, 6 protocols are shortlisted from the protocol library (508a-f), the 6 protocols corresponding to default protocols for an adult whose abdomen is being scanned by CT imaging for the presence of a herniated condition. It will be appreciated that additional or fewer filters may be similarly applied. The scan technologist may then select a final default protocol to follow during the active scan, the selection based on clinical rules that the technologist has to learn and remember. Thus, the protocol selection can be cognitively taxing.

While the depicted example shows the protocols being shortlisted on the computing device of the imaging system, in still other examples, the default protocols may be available through a series of handbooks or manuals and the scan technologist has to refer to paper charts, or quick guide paper workflows, to select and shortlist a default protocol to apply at the time of the scan. Further still, the technologist may have to learn clinical rules specific to the site where the imaging system is being operated. For example, a site may require that the all CT protocols associated with one or more specified attributes (e.g., all CT scans, all adult CT scans, all adult brain CT scans, etc.) follow a specific workflow including calling out to a specified entity (e.g., the radiology department of the site, a doctor at the site, a doctor in the radiology department of the site, etc.) at a specified decision point along the protocol. As an example, a CT perfusion may be added only if a physician of the specified department orders it, after reviewing an initial angiogram scan. Until then, the technologist is expected not to proceed with a scan protocol. The technologist not only has to learn the site specific clinical rules but also has to remember to apply them at the time of the relevant scan. This can add significant cognitive load on the technologist.

Further still, the protocol selections may have to be performed manually on the computing device during the time of a scan. As an example, the scan technologist may first select a default protocol for CT imaging an adult while manually removing all default protocols associated with scanning a child. By selecting for an adult, at least the table motor settings may start to initialize in anticipation of an adult subject. In one example, the technologist may determine the subject's population type based on their age, as indicated in the subject's charts. Then the technologist may select downstream protocols (or protocol branches) for subject size. As an example, there may be generic categories for adult sizes, such as "small", "medium", and "large" and the technologist may select for size based on a visual inspection of the subject, or based on rules defined in a manual, handbook, or paper quick guide. If the technologist decides that the subject is of "medium" size, then they may select downstream protocol branches associated with the subject size while removing protocol branches associated with other sizes (e.g., select "scan-adult, medium" and remove "scan-adult, large", and "scan-adult small"). In the same way, further selections may be sequentially made based on anatomical region being scanned, suspected issue being scanned for, type of contrast being used, etc. The scan technologist operating the imaging system at the time of an active scan may have to refer to paper charts, or quick guide paper workflows, when making the selections. As a result, a significant cognitive load is exerted on the scan technologist which can induce errors in protocol selection. Further, workflows that involve manual changes or require the technologist to remember actions can take time to learn. In addition, there may be variations in decision making due to subjectivity in selection. For example, while one scan technologist may decide that the subject is an adult of medium size, another scan technologist may decide that the same subject is an adult of a large or small size. As such, the selection impacts downstream protocol selections including imaging system settings and subsequent action items to be performed. For example, table motor and gantry settings for a medium adult may be significantly different from those of a small adult. Furthermore, the manual protocol selection may be impacted by the technologist's state of mind at the time of the scan. For example, there may be factors such as fatigue that impact the decisions leading up to and during the scan acquisition. As a result, the cognitive capacity of the scan technologist is not the same at all times of the day. This results in inconsistencies and variations in protocol selection since a decision executed upstream during protocol selection affects downstream protocol branch options.

To avert such errors and inconsistencies while also reducing the cognitive load on the scan technologist, a protocol manager of the computing device of an imaging system (such as protocol manager 234) may enable customized protocols to be generated from the default protocols of the library by authenticated users, the customized protocols embedding within themselves instructions for providing a guided workflow to the technologist at the time of the scan. For example, a protocol manager interface may prompt the operator to input details regarding the subject, such as from the subject's chart (e.g., electronic medical record), and may automatically select an appropriate customized protocol, selection of which may automatically populate the workflow displayed to the operator. The guided workflow may include step-by-step instructions for executing a scan based on site-specific clinical rules in accordance with the selected customized protocol. In addition, by automatically adjusting settings for the imaging system, such as for a CT scanner's gantry, motor, and X-ray source, the time and cognitive load required in selecting them (by a non-authenticated user operating the imaging system at the tie of a new scan) is reduced.

FIG. 6A shows an example view 600 of a protocol manager interface 235 presented by a protocol manager (such as protocol manager 234 of FIG. 2) that may be output on a display device 601 at the onset of a new scan. In one example, display device 601 is a local display device of an imaging system, such as display device 232 of the CT imaging system 200 of FIG. 2. The protocol manager may be executed by the computing device of the imaging system.

Upon initiation of a new scan, the protocol manager may output, on interface 235, a default initiation action item 602. In one example, selection of the default initiation action item by the operator, such as via selection of action box 603, generates a message box 610 which prompts the operator of the imaging system to input subject parameters 604. This enables the subject to be scouted for various attributes. Various subject parameters 604 may be queried. These may include, as non-limiting examples, subject height, weight, age, (suspected) medical condition, and contrast phase being used. In other examples, the subject parameters may be automatically obtained by the system without the user having to manually enter the parameters, such as by querying the patient's electronic medical record. The subject parameters that are output on the interface may be a default set of parameters that are always displayed upon initiation of a new task to scout the subject. Alternatively, the subject parameters may be defined for the protocol manager by an authenticated user. For at least some of the parameters, the message box 610 may include an input area for receiving input regarding the associated parameter of the subject in specified units. For example, by prompting the operator to input the subject's height (in feet and inches), weight (in pounds), and age (in years and months), the protocol manager can determine whether the subject is an adult or a child, and whether they are to be categorized as small, medium, or large. For other parameters, the message box 610 may include a dropdown menu with predefined parameter options. The operator selects one of the options from the dropdown menu. For example, the operator is prompted to select one of the possible anatomical regions that can be imaged by the imaging system, one of the possible medical conditions regions that can be identified by the imaging, and one of the contrast phases that are available for use.

Once these inputs are received by the system, the protocol manager automatically selects a protocol from the protocol library. In one example, the protocol library may be updated to include default protocols as well as modified protocols that were generated by an authenticated user by modifying one or more of the default protocols. Example protocol modifications are elaborated with reference to FIGS. 7-11. The protocol manager is configured to automatically select a protocol from the library of protocols based on the operator input received during patient scouting. FIG. 6B shows another example view 650 of the protocol manager interface 235 after receiving subject scouting input from the operator. The protocol manager identifies a protocol 612 that best matches the information input in message box 610. In the depicted example, the selected protocol is a default protocol, such as a manufacturer installed protocol stored in the protocol library of the imaging system's memory. An operator can then select the shortlisted protocol which results in a workflow being displayed to the operator during the active scan. While the depicted example shows one protocol being shortlisted, in other examples, multiple protocols may be shortlisted. In one example, the shortlisted protocols may be displayed in a ranked order, the protocols ranked based on relevance, popularity, or another attribute defined in the settings of the imaging system. In this way, the protocol manager assists in protocol selection and reduces issues related to operator subjectivity, and associated inconsistencies. In particular, errors in selecting imaging system parameters and settings are reduced. For example, the imaging system settings and parameters may be automatically adjusted and defined based on the modified protocol, without requiring the user performing the scan to manually select settings and manually modify the workflow at the time of a scan.

In addition, the imaging system, e.g., CT scanner, may operate more efficiently because the imaging system is aware, in advance, of the likely X-ray source settings, and image reconstruction parameters needed to complete the scan and the reconstruction.

FIG. 7 shows an example view 700 of a protocol manager interface 235 presented by a protocol manager of an imaging system's computing device to enable an authenticated user to modify a default protocol. The modifications to the default protocol may allow customized protocols to be created for a site by an authenticated user of the site. The default protocol may be one of a plurality of default protocols that are installed in the computing device's memory by a manufacturer of the imaging system. While not shown in the depicted example, the protocol manager may request an authentication key from the operator to verify that they have permission to modify the default protocol. In some examples, an indicator key 720 may be provided to indicate that the protocol is a default protocol.

In the depicted example, the authenticated user has selected default protocol 702 (which in the depicted example is an acute stroke protocol for an adult) by selecting action box 723. Upon selection of the default protocol 702, multiple action items 703 of the protocol are displayed. In particular, each protocol includes multiple action items arranged in a sequence, the action items to be performed in that sequence. The action items of the protocol correspond to a workflow to be executed by another operator during an active scan, such as a non-authenticated user operating the imaging system, the non-authenticated user not permitted to modify the default protocol.

It is to be understood that as used herein, "non-authenticated user" refers to a user that is not authenticated to modify a protocol, where the modified protocol is then stored and available for future scans. However, a non-authenticated user may still be authenticated to perform a scan, view patient medical information, and perform other actions, as well as provide user input that may be used to generate a temporary workflow based on a selected protocol (e.g., by entering patient information, making selection when presented with a decision step, etc.). The authenticated used is authenticated to perform all the actions that the non-authenticated user is permitted to perform, as well as modify a protocol retrieved from a protocol library.

The authenticated user may select an action item from the multiple action items of the protocol for modification, for example by selecting an action box 724. Herein, the selected action item is a non-contrast head scan depicted at 704. Upon selection, a visual attribute of the selected action item 704 (herein a thickness of an interface element displaying the action item) may be changed to indicate that the corresponding action item has been selected. Upon selection of action item 704, a message box 706 may be displayed. The message box 706 may then be populated with modification parameters by the authenticated user. The message box 706 includes, at the top, the action item 704 of the default protocol that was selected for modification. The message box further includes category elements which lists the different category of modifications the authenticated user is able to perform to the selected action item. In the depicted example, two types of category elements are provided including a guidance message element 708 and a decision point element 710. Selection of the guidance message element 708 by the authenticated user indicates that the intended modification to the action item 704 includes a guidance message. The guidance message may include tasks, such as clinical tasks, to be performed at the selected action item of the protocol. Selection of the decision point element 710 by the authenticated user indicates that the intended modification to the action item 704 includes a decision point. The decision point may include a gate or check point seeking user input at the time of an active scan.

Message box 706 further includes a modification element 712 for receiving a content of the modification from the authenticated user. The modification element displayed may be function of the category element selected. Herein, the authenticated user selects decision point element 710, indicating that the intended modification to the action item 704 includes a decision point. Since the category element selection made by the user indicates that the modification is a decision point, the modification element 712 generated includes an area 709 for receiving decision point content, such as a question to be posed to the user that prompts the user to make a response selection (e.g., "Contact radiology department at *5555 and ask if there is a bleed"; "Is there a risk of dissection"; "Is there a bleed in the non-con head"; "Is there metal in the initial scan"). Since this is a decision point, the modification element 712 further includes one or more response elements (herein two, 711, 713) for receiving, from the authenticated user, content regarding predefined responses to the decision point content. For example, response element 711 corresponds to a first (NO) predefined response (e.g., "NO", when a bleed is not identified upon contacting the radiology department, as prompted in area 709) and response element 713 corresponds to a second (YES) predefined response (e.g., "YES", when there is a bleed identified upon contacting the radiology department, as prompted in area 709).

Each response element 711, 713 further includes a response action element wherein the authenticated user can input a task associated with, and coupled/linked to, the response element. In particular, the content of response action element 715 is coupled to the selection of response element 711 while the content of response action element 717 is coupled to the selection of response element 713. This defines the content to be displayed in an action item when the response element 715 is selected (e.g., "Perform CTP with built-in mCTA protocol") versus when the response element 717 is selected (e.g., "terminate scan, delete all remaining recons").

In addition to including content to be displayed upon selection of the corresponding response element, the response action element may also include a link or instructions coupling the response element to a downstream protocol branch, a subset of action items, or another protocol template. The protocol branch or subset of action items may be a portion of the initially selected default protocol, another default protocol, or another modified protocol and may be stored in the protocol library, identifiable by an identity element. Alternatively, instead of linking the response action element to a protocol branch, the user may specify action items, tasks, imaging system settings, etc. Consequently, downstream action items of the modified protocol may be updated. In the depicted example, response action element 715 is coupled to protocol branch #345, causing the modified protocol to be automatically populated with all the action items of protocol branch #345, downstream of action item 704, when response element 715 is selected by a user at the time of a scan. In comparison, response action element 717 is coupled to protocol branch #23, causing the modified protocol to be automatically populated with all the action items of protocol branch #23, downstream of action item 704, when response element 717 is selected by a user at the time of a scan. While the example depicts two response elements and two response action elements, multiple response action elements may be provided as a function of the number of response elements defined by the authenticated user on protocol manager interface 235. As another example, the decision point may query if metal is present in the initial scan, and if yes, the response element triggers a metal artifact reduction protocol.

In addition, message box 706 includes multiple update elements that indicate how the modification to the selected action item is to be implemented. For example, selection of a first update element 714 causes the content of the selected action item to be replaced with the content of the modification element 712. As a result, when the modified protocol is retrieved, the selected action item is modified to display the updated content. As another example, selection of a second update element 716 (as in the depicted example) causes the content of the modification element 712 to be inserted into a new action item that is inserted into the default protocol after the selected action item 704. Selection of a third update element 718 causes the selected action item to be deleted. Still other update elements corresponding to other possible updates may be provided. For example, an update element may be displayed that enables modification of a sequence of the action items in the default protocol. Selection of such an update element may result in a rearrangement of the action items of the selected default protocol such that all the action items of the default protocol are included in the modified protocol, however, in a different sequence.

Due to selection of the second update element 716, the content of the modification element 712 is inserted after the action item 704. As a result, when the modified protocol is retrieved, a decision point is displayed in the workflow, as elaborated at FIGS. 9A-9B. In addition to the decision point, the defined responses corresponding to the response elements are displayed, prompting a user to make a selection. Further, based on the received user selection, subsequent action items of the protocol are changed. A modification to the selected action item 704 results in the default protocol being modified by the protocol manager to a modified protocol which is then stored in the computing device's memory. Further, the modification to selected action item 704 results in corresponding update to a workflow presented to a non-authenticated user when the modified protocol is selected at the time of an active scan. FIGS. 9A and 9B show example workflows that are generated and displayed as a result of the modification of default protocol 702 in FIG. 7. The workflows differ based upon selection of a different response element of a decision point of the modified protocol.

FIG. 8 shows an example view 800 of the protocol manager interface 235 presented by a protocol manager of an imaging system's computing device to enable an authenticated user to modify default protocol 702 (as in FIG. 7). In this example, as in FIG. 7, user selection of selected action item 802 is highlighted via adjustment of an attribute. Responsive to user selection of selected action item 802, a message box 806 is displayed for receiving user input on the requested modification to default protocol 702 at selected action item 802. Similar to FIG. 7, message box 806 includes the selected action item 802, a guidance message box 808, and a decision point box 810.

In the depicted example, since the category element selection made by the user indicates that the modification is a decision point, a modification element 812 generated includes an area 809 for receiving decision content. The authenticated user populates the modification element 812 with content including a question (for example, "is time of stroke symptom onset known?"). The user may also populate area 809 with steps to be performed depending on the answer to the question provided in the modification element 812. As shown, a first response element 813 corresponds to an action to be performed when the answer to the posed question is YES (e.g., "skip CT Perfusion and proceed to Post-contrast Head"), and a second response element 815 corresponds to an action to be performed when the answer to the posed question is NO (e.g., "proceed to CT Perfusion").

In addition, message box 806 includes multiple update elements that indicate how the modification to the selected action item is to be implemented. For example, selection of a first update element 814 causes the content of the selected action item to be replaced with the content of the modification element 812. As a result, when the modified protocol is retrieved, the selected action item is modified to display the updated content. As another example, selection of a second update element 816 (as in the depicted example) causes the content of the modification element 812 to be inserted into a new action item that is inserted into the default protocol after the selected action item 802. Selection of a third update element 818 causes the selected action item to be deleted. Still other update elements corresponding to other possible updates may be provided. For example, an update element may be displayed that enables modification of a sequence of the action items in the default protocol. Selection of such an update element may result in a rearrangement of the action items of the selected default protocol such that all the action items of the default protocol are included in the modified protocol, however, in a different sequence.

A modification to the selected action item 802 results in the default protocol being modified by the protocol manager to a modified protocol which is then stored in the computing device's memory. Further, the modification to selected action item 802 results in corresponding update to a workflow presented to a non-authenticated user when the modified protocol is selected at the time of an active scan.

FIG. 11 depicts modified protocol 1100 that is generated by an authenticated user modifying default protocol 702 on a protocol manager, as shown in FIG. 7. Modified protocol may be stored in the computing device's memory, such as in a protocol library which also includes default protocol 702. Upon selection and retrieval of the modified protocol 1100 by a user, who may be an authenticated or a non-authenticated user, the action items of modified protocol 1100 are displayed. An updated indicator key 1120 is displayed next to the modified protocol to indicate that the protocol is modified from a default protocol (compare to indicator key 720 of default protocol 702 in FIG. 7). In addition, a physical attribute of the modified action item(s) 1108 is changed, such as a color of the message box border, or a thickness of the message box border. As an example, the protocol manager may display the modified action item with a blue border while all other unmodified action items are displayed with a grey border.

An action item indicator key 1106 is also displayed next to the modified action item 1108 to identify the specific action item that was modified from the default protocol. Further, a notification 1102 may notify the user of the modification history such as a date and time when action item 1108 was generated, as well as the identity of the authenticated user who modified the default protocol to generate action item 1108 (e.g., "last modified by Dr. Smith on 3/21/2019 at 3:21 pm PST"). Furthermore, notification 1102 may include a history box 1104 showing the original version of the action item, as it was in the default protocol. If the modified protocol, and action item 1108, has been modified multiple times, then the notification 1102 may include the history of all modifications since the default state, as well as all the interim modified versions in addition to the default version in the default protocol. It is to be understood that the history of modifications by the authenticated user described here may be different than the inputs/decisions entered by the non-authenticated user described above, and that the history of modifications by the authenticated user may be saved in a different location, used for different purposes, and so forth.

As a result, when the modified protocol is retrieved during a scan, the user is made aware that the protocol is a modified one. Further, it allows an authenticated user reviewing the protocols to assess the modifications made to the default protocol, such as to determine a success or performance rate of the modified protocol relative to the default protocol.

In FIG. 10, at the time of an active scan, a non-authenticated may be presented with a workflow 1000 corresponding to modified protocol 1002 by the protocol manager on interface 235. The modified protocol 1002 includes new action items such as action item 1004 following action item 802 of the modified protocol of FIG. 8, and this is updated in workflow 1000. New action item 1004 includes the content of one of the response elements shown in FIG. 8, specifically the content of response element 813 which is displayed upon the user selecting YES to the question posed after action item 802 (e.g., "is time of stroke symptom onset known?"). The workflow 1000 displayed on the interface 235 also includes check boxes 1006 that the non-authenticated user can select based on the user's progress through the workflow. At least one check box is provided for each action item of the workflow.

In FIG. 9A, at the time of an active scan, a non-authenticated user may be presented with a workflow 900 corresponding to modified protocol 902 by the protocol manager on interface 235. The workflow 900 displayed on the interface 235 also includes check boxes 904 that the non-authenticated user can select based on the user's progress through the workflow. At least one check box is provided for each action item of the workflow. The modified protocol 902 includes an updated action item 906 inserted into the default protocol 702 (of FIG. 7). Updated action item 906 includes the content of modification element 712 that was input by the authenticated user during the protocol modification (e.g., "Contact radiology department at *5555 and ask if there is a bleed"). The new action item 906 prompts the user to, at the time of the scan, make a selection by providing input at a response element. In the example of FIG. 9A, the user has selected response element 908.

Upon completion of the selection, the protocol manager automatically populates the workflow 900 with downstream action items specified in the modified protocol. In this instance, selection of response element 908 causes all action items downstream of original action item 704 of default protocol 702 to be deleted while populating the workflow with action items 910 retrieved from the protocol branch linked to response element 908 (e.g., action items related to performing CTP with built-in mCTA).

In comparison, in FIG. 9B, selection of response element 912 causes all action items downstream of original action item 704 of default protocol 702 to be deleted while populating the workflow with action item 914 retrieved from the protocol branch linked to response element 906 (e.g., "terminate scan, delete all remaining recons").

It will be appreciated that in each instance where an action item of a default protocol is modified, the workflow may also be modified to update imaging system settings relative to default settings. For example, a modified action item of the workflow that includes termination of the scan may automatically, without requiring user input, disable one or more motors of the imaging system, such as the table motor or gantry motor. As another example, a modified action item of the workflow that includes operating a CTP scan may automatically, without requiring user input, adjust the motor settings (e.g., power, speed, output, etc.) to the settings for a CTP scan which may be different from the current settings of the imaging system.

As another example, a CT Abdomen Pelvis exam may be conducted for evaluation of endograft. There are four different types of malfunctions/leaks that may be evaluated at different times (from arterial to late venous, approximately 25 seconds to 80 seconds). Frequently, facilities build multiple protocols that scan at different times, gantry speed, and/or dose factors. This decision point allows for multiple exam scan parameters and titles to be built into one protocol management that can then be selected in real time, thus reducing protocol clutter and reducing tech error.

A modified/decision-tree based protocol for CT Abdomen Pelvis may begin with a scout scan (e.g., anterior posterior (AP) and lateral scout). A second step of the protocol may include a non-contrast/unenhanced scan to cover the anatomical region prior to a contrasted scan. After the non-contrast scan, the decision tree would execute to allow selection of a desired contrasted study. This could include multiple scans over the abdomen/pelvis at a combination of scan times/parameters. For example, the decision tree may present four scan options. These could be broken off into separate protocols to include a combo of each phase, or all phases at this point in the decision tree/protocol management. The first scan option may include an angiographic phase, approximately 25 second scan for type 1 endograft link, full dose, faster table travel to follow contrast bolus. A second scan option may include an intermediate delay, 35-40 seconds for type 2 endograft leak, full dose, slower table travel than computed tomography angiography (CTA). A third scan option may include a 55-70 second delay to evaluate type 3 endograft leak, potentially lower dose than previous two scan options. A fourth scan option may include 85 second plus a delay for type 4 endograft leak, slower table movement than the first scan option, potential for dose adjustment. The user may select which scan option to execute based on questions provided in the decision tree, and the user may make a selection based at least in part on the findings of the non-contrast scan and/or other relevant patient findings. Once a scan option is selected, the protocol for that scan option may be retrieved and presented to the user as part of the workflow for the user to follow to conduct the relevant scan. By doing so, the decision tree based approach described herein may reduce the cognitive load on the technologist by assisting the technologist with the selection of the most relevant scan protocol and/or scan protocol branches and automatically populating a workflow with the selected protocol/branches. During execution of the exam, the technologist may be presented an interface that shows the technologist the overall progress through the exam and/or selections that may be made from a menu.

The modifications of FIGS. 7-11 may, in one example, be implemented by the execution of method 300 of FIG. 3. Turning now to FIG. 3, an example method 300 is shown for modifying a default protocol of the protocol library based on input received from an authenticated user. The method may be executed by a protocol manager (such as protocol manager 234) on a computing device of an imaging system. In one example, the computing device is a local device of a CT imaging system. The method enables a customized protocol to be generated and stored in the protocol library for use during subsequent scans.

At 302, the protocol manager receives an authentication key from a user interacting with the protocol manager. In one example, the authentication key is received via a user input device, such as input device 232. The input device may be a keyboard or touchscreen, for example.

At 304, the protocol manager determines if the user is authorized to modify protocol(s) stored in the computing device based on the received authentication key. For example, if the received authentication key has the appropriate security elements, then it may be determined that the user is authorized to modify the protocols. The protocols that can be modified may be one or more default protocols of the imaging system, such as those installed by a manufacturer, as well as one or more previously modified protocols. The default and modified protocols may be stored in a protocol library of the computing device's memory.

If the user is not an authenticated user, such as when the authentication key is not acceptable, the protocol management method moves to 306 where the protocol manager determines if a new scan task has been requested. A user may request a new scan task by selecting a new scan task via an operator console. Upon selection of a new scan task, a new scan is initiated at 308 with the protocol manager retrieving a protocol and displaying a guided workflow to the non-authenticated user in accordance with the retrieved protocol. As elaborated with reference to the example of FIGS. 6A-6B, and detailed in the method of FIG. 4, a protocol manager may, via an interface, seek input from the user regarding one or more attributes of the subject that is being scanned at the new scan task. The protocol manager may then automatically retrieve a protocol from a library of protocols, selected based on the received input, and generate a workflow in accordance with the action items of the retrieved protocol. The retrieved protocol may be a default protocol, such as one installed by the manufacturer. Alternatively, the retrieved protocol may be a modified protocol, such as one modified by an authenticated and authorized user. The method then exits. If a new scan is not requested and the user is not authenticated, then at 309, the user is not allowed to modify any of the protocols in the protocol library. The method then exits.

If the user is authenticated at 304, then at 310, the method includes displaying, on a display device of the computing device of the imaging system, the default protocols available in the protocol library and receiving a user selection of a default protocol to modify. In one example, the protocols may be displayed in the protocol library including tags and filters, as shown in FIG. 5. It will be appreciated that while the method of FIG. 3 discusses modification of default protocols, in further examples, all available protocols including all default and all modified protocols may be displayed to the authenticated user and user selection of any of the available protocols for modification is received. In one example, the display device may be a local display device, such as a monitor coupled to a CT scanning system. However, in other examples, the display device may be a remote display device coupled to a server (e.g., a central picture archiving and communications system (PACS), clinical information system (CIS), hospital information system (HIS), or radiology information system (RIS) server), the server connected to the imaging system over a network.

At 312, a user selection is received via an operator console communicatively coupled to the computing device of the imaging system, such as a keyboard or touchscreen device. The user selection may in the form of an input from the authenticated user indicative of a protocol from the library of protocols that the user wishes to modify. As one example, the user may select a protocol from the library by selecting an action box juxtaposed next to the target protocol on the protocol manager interface (such as action box 603 of FIGS. 5 and 6A).

Upon receiving a selection of the protocol, at 312, the protocol manager may confirm if the authenticated user wishes to modify the selected protocol. As an example, a message box may pop-up querying the user if the user wishes to modify the selected protocol. If the user confirms the request, then at 314, the protocol manager may display all the action items of the selected default protocol, in their defined default sequence and prompt the authenticated user to select a location for modification of the default protocol. For example, an action box may be displayed next to each action item of the selected default protocol, and the authenticated user may select an action item where a modification is to be entered into the selected default protocol. FIG. 7 shows an example wherein action item 704 of default protocol 702 is selected by an authenticated user on a protocol manager interface to indicate the location of modification of the protocol. As used herein, the location of modification may refer to an action item of the default protocol that the authenticated user aims to modify (e.g., update the content of, change the sequence of, or delete). As another example, the location of modification may refer to an action item of the default protocol after (or before) which the authenticated user aims to insert another action item.

At 316, the protocol manager may prompt the user to select a type of modification the user wishes to make. For example, responsive to selection of an action item at 314, the protocol manager may output a message box, such as pop-up message box 706 of FIG. 7. The protocol manager may display one or more category elements in the message box, each category element indicative of a type of modification, such as a guidance message 317a, a decision point 317b, and an alert 317c. The user is prompted to select a category element from the displayed elements, such as via selection of corresponding action boxes.

At 318, the protocol manager receives content pertaining to the modified action item. For example, the user is prompted to input content into a modification element of the message box. As elaborated with reference to the examples of FIGS. 7 and 8, the modification element displayed to the user may be a function of the category element. A modification element displayed when the modification is of a guidance message category may include an area for receiving guidance message content from the authenticated user with which to modify the selected action item. The authenticated user populates the modification element (such as element 712 of FIG. 7) with content including one or more tasks to be performed at the selected action item (for example, "Use Dr. XYZ's special. Apply perfusion sampling or time ABC" when the user selects to enter a guidance message). As such, the modification element of a guidance message includes content that is accepted and does not require user input at the time of an active scan.

A modification element displayed when the modification is of a decision point category may include an area for receiving decision point content, such as a question to be posed to a user at the time of scan, wherein the question prompts the user (which may be a non-authenticated user) to make a response selection (e.g., "Contact radiology department at *5555 and ask if there is a bleed" or "Is there a risk of dissection" or "Is there a bleed in the non-con head"). In the case of a decision point category, as shown at FIG. 8, the modification element further includes one or more response elements for receiving, from the authenticated user, content regarding predefined responses to the decision point content. These may include, for example, standard response elements, such as "yes" and "no" response elements for all decision points. Still other response elements may be customized based on the content of the decision point.

At 320, the protocol manager receives user input regarding action elements coupling the modified action item to downstream protocols, protocol templates, or subsets of a protocol. For example, when the modification is a guidance message category, the modification element may include a task associated with, and coupled or linked to, the modification element and content to be displayed in the modified action. In addition to including content to be displayed at the modified action item, the modification action element may also include a link or instructions coupling the modified action item to a downstream protocol branch, a subset of action items, or another protocol template.

When the modification includes a decision point category, each response element may include a response action element wherein the authenticated user can input a task associated with the corresponding response element. For example, when the modification includes a decision point category, each response element may include a response action element wherein the authenticated user can input a task associated with, and coupled or linked to, the response element. The response action element associated with the response element defines the content to be displayed in a modified action item when a given response element is selected (e.g., "Perform CTP with built-in mCTA protocol" or "Terminate scan, delete all remaining recons"). In addition to including content to be displayed upon selection of the corresponding response element, the response action element may also include a link or instructions coupling the response element to a downstream protocol branch, a subset of action items, or another protocol template.

The protocol branch or subset of action items may be a portion of the initially selected default protocol, another default protocol, or another modified protocol and may be stored in the protocol library, identifiable by an identity element. Alternatively, instead of linking the response action element to a protocol branch, the user may specify action items, tasks, and/or imaging system settings (e.g., motor speed of gantry and table motor, X-ray source voltage and current settings, etc.). Consequently, downstream action items may be changed from the default protocol to generate a modified protocol. It will be appreciated that steps 312 to 320 may be iterated until the authenticated user has made all the desired modifications to the selected default protocol.

At 322, once all modifications to action items are received, the protocol manager may output a modified protocol including the one or more modified action item(s). The modified protocol may include an identification key indicating that the protocol has been modified from a default version. In addition, the modified protocol may be time stamped to include history details, such as when the protocol was last modified, who the modifier was, which action items of the protocol have been modified, etc. At 324, the protocol manager may also change a visual attribute of the modified action item to specify the incidence of a modification. For example, the modified action item of the modified protocol may be indicated with an alternate color, alternate font, alternate background, etc. The modified protocol is then stored in the computing device's memory. In addition, responsive to the authenticated user modifying the default protocol, a notification may be pushed out to the manufacturer of the imaging system, the notification including the modified protocol and highlighting the changes relative to the default protocol that was modified to generate the modified protocol.

From 322, the method moves to 326, where the authenticated user is queried if a new scan task is to be initiated. If yes, then at 328, the modified protocol is retrieved and a guided workflow is provided in accordance with the modified protocol. If a new scan task is not selected, then at 330, the protocol library is updated to include the modified protocol. The method then exits.

In this way, the modification of the protocol causes modification of the workflow as well as the operation of the imaging system (such as the CT scanner) itself since the modified protocol includes system parameters to be applied for the imaging system at the time of the new scan.

It will be appreciated that the protocol manager may be configured to output different interfaces to the authenticated user as compared to the non-authenticated user. Likewise, the interface that is output by the protocol manager during scan set-up (such as at the time of patient scouting) may be different from the interface that is output at the time of an active scan, both of which may be distinct from the interface that is output at the time of protocol modification. Example interfaces are shown with reference to FIGS. 6A-9B. In particular, a first user interface, such as the interface of FIGS. 6A-6B, is displayed to the non-authenticated user at the time of scan initiation. Therein, input is requested regarding subject attributes so as to enable automatic patient scouting. This reduces user-induced errors, such as errors in patient size determination, which can result in downstream errors in protocol selection. A second user interface, such as the interface of FIGS. 9A and 9B, is displayed to the non-authenticated user at the time of a scan after automatic protocol selection. A third user interface, such as the interface of FIGS. 7 and 8, is displayed to the authenticated user at the time of protocol modification.

Turning now to FIG. 4, an example method 400 is shown for retrieving a modified protocol and generating a guided workflow associated with the modified protocol, the guided workflow displayed to a non-authenticated user at the time of a new scan. The method of FIG. 4 may be incorporated into the method of FIG. 3, such as at step 328.

At 402, method 400 confirms that a new scan is to be initiated. If a new scan is not to be initiated, the method ends. If a new scan is confirmed, then at 404, the method includes prompting a user, such as a non-authenticated user performing the scan, to provide input including parameters related to the new scan. In one example, at 406, questions and/or notes may be displayed, such as via a message box on a protocol manager interface, prompting the user to acknowledge or fill out details pertaining to subject attributes, at onset of the scan. As shown with reference to FIGS. 6A-6B, the protocol manager may output, on the interface, a message box which prompts the operator of the imaging system to input subject parameters. This enables the subject to be scouted for various attributes. Various subject parameters may be queried such as subject height, weight, age, (suspected) medical condition, and contrast phase being used. The subject parameters that are output on the interface may be a default set of parameters that are always displayed upon initiation of a new task to scout the subject. Alternatively, the subject parameters may be defined in the settings of the protocol manager by an authenticated user. For at least some of the parameters, the message box may include an input area for receiving input regarding the associated parameter of the subject in specified units. For example, the user may be prompted to input the subject's height (in feet and inches), weight (in pounds), and age (in years and months). For other parameters, the message box may include a dropdown menu with predefined parameter options. The user is prompted to select one of the options from the dropdown menu. For example, the operator is prompted to select a possible anatomical region that can be imaged by the imaging system, a suspected medical condition to be assessed by the imaging, and one of the contrast phases that are available for use.

At 408, the method includes retrieving a protocol associated with the new scan based on the received user input. Once the inputs are received from the user, the protocol manager automatically selects a protocol from the protocol library. In one example, the protocol library may be updated to include default protocols as well as modified protocols that were generated by an authenticated user and the protocol manager is configured to automatically select a protocol from the library of protocols based on the input received during patient scouting. The protocol manager identifies a protocol that best matches the input information.

The retrieved protocol may include, at 410, action items that include adjusting imaging system settings in accordance with settings specified in the retrieved protocol, such as motor settings, gantry settings, X-ray source settings, etc. The retrieved protocol may additionally or alternatively include, at 412, action items that include adjusting a scan prescription, reconstruction settings, etc., based on retrieved protocol.

At 414, the method includes generating a guided workflow including a sequence of action items to be executed by a user during an active scan based on the retrieved protocol. For example, at the time of an active scan, a non-authenticated user may be presented with a workflow corresponding to a modified protocol by the protocol manager on an interface. Each action item of the modified protocol, including all modified or new action items, are correspondingly displayed in the workflow. The content of a message box that was input by the authenticated user during the protocol modification is represented by an action item in the workflow with the corresponding content. At 416, content associated with each action item of the protocol are displayed in the workflow in the corresponding sequence. At 418, the user is prompted to provide input associated with an action item of the protocol, such as may occur when the action item includes a decision point and user input is solicited, as shown in FIGS. 7 and 8.

At 420, the method includes automatically selecting downstream protocol template(s)/branches/subsets and populating the workflow displayed to the user with subsequent or downstream action items based on the received user input. When the action item includes a decision point, based on a response element selected by the user, the protocol manager automatically populates the workflow with downstream action items specified in the modified protocol. As an example, selection of a first response element populates the workflow with a first set of action items retrieved from the protocol branch linked to the first response element (e.g., action items related to "performing CTP with built-in mCTA"). The associated first set of action items may also define system parameters to be automatically applied when the first response element is selected. For example, during the scan, when a workflow corresponding to the modified protocol is displayed, if user input indicates that a "bleed is not identified" response element is selected, the X-ray source voltage and current settings, gantry speed, etc., required for performing a computed tomography perfusion (CTP) scan with multiphase computed tomography angiography (mCTA) may be automatically applied. As a result, the imaging system settings may be automatically adjusted to prepare the scanner for a CT perfusion scan with mCTA, reducing delays and errors (such as user-induced delays and errors) associated with the protocol change. As an example, the X-ray source voltage may be increased/decreased from the current setting to the setting required for perfusion scanning. As another example, the gantry position, table position, etc., may be transitioned from the current setting to the setting required for perfusion scanning.

In comparison, selection of a second response element populates the workflow with a second, different set of action items retrieved from the protocol branch linked to the second response element (e.g., "terminate scan, delete all remaining recons"). The associated second set of action items may also define system parameters to be automatically applied when the second response element is selected. For example, during the scan, when a workflow corresponding to the modified protocol is displayed, if user input indicates that a "bleed is identified" response element is selected, the X-ray source voltage and current settings, gantry speed, etc., required for terminating the current scan may be automatically applied. As a result, the imaging system settings may be automatically adjusted to prepare the scanner for completing the scan. As an example, the X-ray source voltage may be decreased, the gantry and table may be moved to a default position, motor speeds may be reduced, etc.

At 422, the imaging system is operated in accordance with settings defined in the action items of the selected protocol to complete the scan. The scan includes acquiring imaging information (such as projection data) that is usable to reconstruct one or more images. The imaging information acquired during the scan are saved upon completion of the scan.

Various subject parameters as well as various parameters of the medical imaging session may be adjusted during the scan based on the settings defined in the action items of the modified protocol retrieved during the scan, and the workflow displayed at the scan. These may include, for example, pausing image acquisition and/or outputting notifications to the subject and/or operator when subject movement is detected. Further, video stream(s) from an imaging sensor may be displayed during the scan and video stream settings (such as an angle of image capture of the imaging sensor) may be adjusted based on the settings defined in the modified protocol. For example, in the case of head computed tomography perfusion (CTP), if the head moves more than 1 cm from one pass to another, then the acquisition may be terminated and the scanner may be set up to repeat that CTP series. This motion may be detected by a 3D infrared video camera feed or by other mechanisms.

The information from the image sensor may be usable by an image sensor data processor to perform tracking of one or more subjects in the field of view of the image sensor. In one example, the image information (e.g., depth information) may be used to perform skeletal tracking, wherein a plurality of joints of the subject are identified and analyzed to determine movement, pose, position, etc., of the subject. The location of the joints during skeletal tracking may be used to determine the subject parameters described above.

The systems and methods described herein may provide for defining and implementing new taxonomy. Rather than a collection of disjointed protocols, the systems and methods described herein may, as a first step (in protocol manager, for example), organize the protocols in the format of a decision tree. Then at scan time, throughout the various steps of the acquisition, the user input and on based on the findings on the fly, the user answers questions and the answers to the questions trims the tree. This trimmed tree has the effect of guiding the user to the next step.

Further, while the systems and methods described herein are directed to allowing modification of a default or already modified scanning protocol, and then presenting the modified scanning protocol to a user so that the user may carry out a diagnostic imaging scan according to the modified scanning protocol, the modified protocols described herein may not be limited to providing information for a user to follow during a scan. Rather, it may be desirable to determine automatically how to split a particular scan/exam out for billing purposes before the scan starts. For example, the protocol manager described herein may be able to initiate an exam split (for billing code purposes) at any time during the scan protocol (during, or at the end), thereby providing an "on the fly/retrospective exam split". This on-the-fly exam split may be facilitated via questions provided in the modified protocol. For example, at scan time the non-authenticated user may select from a trimmed list of billing departments/codes where the trimmed list may be entered/downselected in the protocol manager by the authenticated user.

As an example, the acute stroke protocol described above may include charge/bill codes that include a head scan without contrast, a computed tomography perfusion (CTP) of the head/desired head anatomy, and a computed tomography angiography (CTA) scan of the full head and neck vascular anatomy. The final decision on which scans to preform is often done as the patient is on the scan table by the attending neurology team. The neurology team will come with the stroke patient to the scanner and perform an initial physical evaluation. Sometimes the decision to move forward with or discontinue a full stroke scan procedure comes after the performance and evaluation of the head scan without contrast. There are often three different clinical scenarios surrounding ordering and scanning full or partial scans in CTP at Stroke Centers: a) head without contrast, CTP head, and CTA head and neck; b) head without contrast and CTA head and neck; and c) head without contrast only.

Having a reactive exam split functionality would allow for whichever exam sequence was done to be connected to the proper charge code or codes (head without charge plus CTA head and neck). Another benefit of a reactive exam split functionality would be in a scenario where potentially only a head without scan was ordered initially but when the patient was on the table additional scans were ordered on that patient (a CTP head and CTA head and neck were ordered after patient was on table and single previous order had already been selected.) This functionality would identify all exams that were ordered subsequently and allow the tech to assign to proper exam code at the time of scan or utilize existing prospective exam split functionality to have system assign to proper exam code by using existing scan protocols.

The technical effect of displaying a protocol manager interface that prompts a non-authenticated user to input subject parameters and automatically selects a protocol for the subject is that the cognitive load on the user, such as a scan technologist, can be reduced, especially in trauma use cases where protocol selection can be a critical step. In addition, the approach better enables the management of multiple protocols for a particular suspected clinical problem (e.g., a stroke). For example, manual on-the-fly changes to a protocol by the non-authenticated user are reduced. By enabling automatic selection of an appropriate protocol, inconsistencies in workflow and protocol selection due to user subjectivity and user state of mind (such as due to the time of day or shift at which the scan is being performed) are reduced. By increasing consistency, diagnostic quality of the obtained images may be increased. In addition, the user is not required to memorize specific tasks or specific contact information. Further, by displaying a workflow that is based on the action items of the selected protocol, guidance can be embedded into the protocol, reducing the need for supplementary education and training of a scan technologist to educate them about where to stop and revisit protocols, etc. Costs associated with training efforts and creation of manuals and handbooks is also reduced. In addition, scanning consistency is improved. In particular, for a given protocol, the same workflow is presented independent of the user performing the scan. Likewise, for a given combination of subject parameters, the same protocol is selected, independent of the user performing the scan. Furthermore, a record of the workflow that is performed can be documented for posterity and future analysis and review. For example, it can be documented that the technologist called the stroke radiologist at the site and confirmed a bleed condition before proceeding with a mCTA scan.

The technical effect of displaying another user interface to an authenticated user is that default protocols can be customized at a site to account for site-specific clinical rules. By enabling the authenticated user to insert clinical decision trees or embed specific guidance messages at one or more action items of a given protocol, new scan prescriptions including new reconstruction processes can be generated that are improved over the default protocol. As such, this may allow the total number of protocols to be reduced. For example, instead of requiring multiple flavors of a given protocol to account for various possible scenarios, a single protocol can be generated with a decision point that automatically links a particular downstream protocol (or protocol "flavor") with a specified response to the decision point. By automatically updating the workflow displayed at a first interface to the non-authenticated user based on the protocol modifications received from the authenticated user, at a second interface, protocol management is improved.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   a display; and
   a computing device operably coupled to the display and storing instructions executable to:
   output, to the display, a protocol manager interface including a default protocol for an imaging system, the default protocol including one or more displayed action items to be executed in a sequence during an imaging scan by the imaging system, at least a portion of the one or more action items specifying imaging system parameters for the imaging scan;
   responsive to input from an authenticated user, modify the default protocol including modifying the displayed one or more action items and/or the sequence;
   store the modified protocol in a memory of the computing device; and
   responsive to a subsequent request to perform the imaging scan, retrieve the modified protocol and operate the imaging system in accordance with the modified protocol, wherein the imaging system includes a computerized tomography imaging system and wherein the modified protocol includes imaging system parameters including gantry motor setting, table motor settings, and X-ray source voltage and current settings.

2. The system of claim 1, wherein the default protocol is a manufacturer installed default protocol.

3. The system of claim 2, wherein the computing device includes further instructions executable to:
   responsive to the authenticated user modifying the default protocol, send a notification to the manufacturer of the imaging system, the notification including the modified protocol; and
   operate the imaging system in accordance with imaging system parameters defined in the modified protocol.

4. The system of claim 1, wherein the subsequent request to perform the imaging scan is received from a non-authenticated user.

5. The system of claim 4, wherein the computing device includes further instructions executable to:
   request an authentication key;
   responsive to receiving an authentication key of the authenticated user, allow modification of the default protocol by the authenticated user; and
   responsive to receiving an authentication key of a non-authenticated another user, restrict modification of the default protocol by the non-authenticated user.

6. The system of claim 5, wherein the computing device includes further instructions executable to:
   responsive to the subsequent request to perform the imaging scan, output, to the display or another display operably coupled to the computing device, the protocol manager interface including a workflow comprising the one or more displayed action items of the modified protocol.

7. The system of claim 5, wherein the protocol manager interface displayed for receiving input from the authenticated user is distinct from the protocol manager interface displaying the workflow to the non-authenticated user.

8. The system of claim 6, wherein the input from the authenticated user includes selection, on the protocol manager interface, of an action item from the one or more displayed action items, and wherein the computing device includes further instructions executable to:
   responsive to the input from the authenticated user,
     display a message box associated with the selected action item;
     receive content in the displayed message box from the authenticated user;
     automatically display the received content in the selected action item while removing existing content from being displayed in the selected action item; and
     when performing the imaging scan, output the workflow with the selected action item displaying the received content.

9. The system of claim 8, wherein the received content specifies one or more new action items linked downstream of the selected action item, and wherein the computing device includes further instructions executable to:
   upon receiving the content, automatically remove all action items of the default protocol downstream of the selected action item;
   populate the modified protocol with the one or more new action items displayed downstream of the selected action item; and
   when performing the imaging scan, output the workflow with the one or more new action items displayed downstream of the selected action item.

10. The system of claim 8, wherein the displayed message box further includes category elements categorizing the modification to the selected action item, the category elements including at least a first category element associated with a guidance message and a second category element associated with a decision point, wherein the displayed message box prompts the authenticated user to select one of the first and second category element, and wherein when the second category element is selected, the received content includes at a first set of new action items associated with a first response element of the decision point and a second, different set of new action items associated with a second response element of the decision point.

11. The system of claim 10, wherein the computing device includes further instructions executable to:
    at a time of the imaging scan, prompt the non-authenticated user to select one of the first and second response element;
    responsive to selection of the first response element, output the workflow with the first set of new action items displayed downstream of the selected action item while removing all action items of the default protocol downstream of the selected action item; and responsive to selection of the second response element, output the workflow with the second set of new action items displayed downstream of the selected action item while removing all action items of the default protocol downstream of the selected action item.

12. The system of claim 1, wherein the computing device includes further instructions executable to:
store the modified protocol in a protocol library as a function of the default protocol; and
modify a visual attribute of the stored modified protocol including a visual attribute of the one or more modified action items, the modified visual attribute distinguishing the modified protocol from the default protocol in the protocol library.

13. A system, comprising:
a display; and
a computing device operably coupled to the display and storing instructions executable to:
output, to the display, for an authenticated user, a first displayed protocol manager interface including a default manufacturer-installed protocol for an imaging system, the displayed default protocol including one or more action items displayed in a sequence;
responsive to input from the authenticated user, modify, at the displayed first user interface, the default protocol including modifying the one or more displayed action items and/or the sequence; and store the modified protocol along with the default protocol in a protocol library; and
output, to the display or another display operably coupled to the computing device, for the authenticated user or a non-authenticated user, a second protocol manager interface including a workflow displayed during the imaging scan, the displayed workflow comprising the one or more displayed action items of the modified protocol, wherein the imaging system is a computerized tomography imaging system, wherein the modified protocol includes imaging system parameters including gantry motor setting, table motor settings, and X-ray source voltage and current settings; and wherein the computing device includes further instructions executable to automatically operate the imaging system in accordance with the imaging system parameters defined in the modified protocol during the imaging scan.

14. The system of claim 13, wherein the computing device includes further instructions executable to:
receive, on the first user interface, the input from the authenticated user before the imaging scan, including a selection of an action item, for modification, from the one or more action items of the default protocol, new content with which to modify the selected action item, and a set of new action items linked to the selected action item, the set of new action items including action items from another default protocol or another modified protocol; and
display on the second user interface, during the imaging scan, the workflow with prior content of the selected action item replaced with the new content, and with action items of the default protocol downstream of the selected action item replaced with the set of new actions items.

15. The system of claim 14, wherein the computing device includes further instructions executable to:
display, on the first and second user interface, the selected action item with a visual attribute that is different from the visual attribute of remaining unselected action items of the modified protocol; and
in response to input from the authenticated or non-authenticated user, display a comparison of the selected action item of the default protocol with the selected action item of the modified protocol.

16. The system of claim 13, wherein the computing device includes instructions executable to: responsive to the authenticated user modifying the default protocol, send a notification to the manufacturer of the imaging system, the notification including the modified protocol.

17. A method for a computed tomography (CT) imaging system, comprising:
displaying a default protocol defining a default workflow for operating the CT imaging system during a scan, the default protocol including one or more action items executed in a sequence; at least a portion of the one or more action items specifying imaging system parameters for the imaging scan;
receiving, from an authenticated user, modifications to an action item selected from the one or more actions items of the default protocol, the modifications changing the default workflow;
generating a modified protocol based on the received modifications; and
during the scan, retrieving the modified protocol;
displaying a modified workflow corresponding to the modified protocol; and
operating the CT imaging system in accordance with the modified protocol, wherein the modified protocol includes CT imaging system parameters including a gantry motor setting, a table motor setting, X-ray source voltage, and X-ray source current.

18. The method of claim 17, wherein displaying the modified workflow includes:
replacing a content of the selected action in the default protocol with content received as input from the authenticated user in the modified protocol; and
replacing action items downstream of the selected action item in the default protocol with new action items received as the input from the authenticated user in the modified protocol.

* * * * *